United States Patent
Elenko et al.

(10) Patent No.: US 10,369,144 B2
(45) Date of Patent: Aug. 6, 2019

(54) METHODS AND COMPOSITIONS FOR TREATMENT OF DISORDERS AMELIORATED BY MUSCARINIC RECEPTOR ACTIVATION

(71) Applicant: PureTech Health LLC, Boston, MA (US)

(72) Inventors: Eric Elenko, Boston, MA (US); Philip E. Murray, III, Somerville, MA (US); Andrew C. Miller, East Walpole, MA (US)

(73) Assignee: PureTech Health LLC, Boston, MA (US)

( * ) Notice: Subject to any disclaimer, the term of this patent is extended or adjusted under 35 U.S.C. 154(b) by 0 days.

(21) Appl. No.: 16/289,165

(22) Filed: Feb. 28, 2019

(65) Prior Publication Data

US 2019/0192500 A1  Jun. 27, 2019

Related U.S. Application Data

(63) Continuation of application No. 15/400,108, filed on Jan. 6, 2017, now Pat. No. 10,238,643, which is a continuation of application No. 15/161,840, filed on May 23, 2016, now abandoned, which is a continuation of application No. 14/534,698, filed on Nov. 6, 2014, now abandoned, which is a continuation of application No. 13/858,985, filed on Apr. 9, 2013, now abandoned, which is a continuation of application No. 13/592,480, filed on Aug. 23, 2012, now abandoned, which is a continuation of application No. 13/348,057, filed on Jan. 11, 2012, now abandoned, which is a continuation of application No. 12/840,980, filed on Jul. 21, 2010, now abandoned.

(60) Provisional application No. 61/282,658, filed on Mar. 15, 2010, provisional application No. 61/213,853, filed on Jul. 22, 2009.

(51) Int. Cl.

| | | |
|---|---|---|
| A61K 31/46 | (2006.01) | |
| A61K 9/48 | (2006.01) | |
| A61K 31/4439 | (2006.01) | |
| A61K 31/222 | (2006.01) | |
| A61K 31/4025 | (2006.01) | |
| A61K 31/4178 | (2006.01) | |
| A61K 31/438 | (2006.01) | |
| A61K 31/44 | (2006.01) | |
| A61K 31/4725 | (2006.01) | |
| A61K 45/06 | (2006.01) | |
| A61K 31/138 | (2006.01) | |

(52) U.S. Cl.
CPC ........... *A61K 31/46* (2013.01); *A61K 9/48* (2013.01); *A61K 9/485* (2013.01); *A61K 9/4825* (2013.01); *A61K 9/4858* (2013.01); *A61K 9/4866* (2013.01); *A61K 9/4891* (2013.01); *A61K 31/138* (2013.01); *A61K 31/222* (2013.01); *A61K 31/4025* (2013.01); *A61K 31/4178* (2013.01); *A61K 31/438* (2013.01); *A61K 31/44* (2013.01); *A61K 31/4439* (2013.01); *A61K 31/4725* (2013.01); *A61K 45/06* (2013.01)

(58) Field of Classification Search
CPC combination set(s) only.
See application file for complete search history.

(56) References Cited

U.S. PATENT DOCUMENTS

| | | |
|---|---|---|
| 4,647,580 A | 3/1987 | Roszkowski |
| 5,043,345 A | 8/1991 | Sauerberg |
| 5,480,651 A | 1/1996 | Callaway |
| 5,744,476 A | 4/1998 | Locke |
| 5,852,029 A | 12/1998 | Fisher |
| 6,423,842 B1 | 7/2002 | Grewal |
| 7,049,321 B2 | 5/2006 | Fisher |
| 7,410,978 B2 | 8/2008 | Kidane |
| 7,491,715 B2 | 2/2009 | Ek |
| 7,517,871 B2 | 4/2009 | Ek |
| 7,524,965 B2 | 4/2009 | Colson |
| 7,550,454 B2 | 6/2009 | Ek |
| 7,622,461 B2 | 11/2009 | Ek |
| 7,666,894 B2 | 2/2010 | Paborji |
| 7,678,821 B2 | 3/2010 | Paborji |
| 7,781,472 B2 | 8/2010 | Paborji |

(Continued)

FOREIGN PATENT DOCUMENTS

| | | |
|---|---|---|
| DE | 19612504 | 8/1997 |
| EP | 0813870 | 12/1997 |

(Continued)

OTHER PUBLICATIONS

Arehart-Treichel, "GABA Targeted for Study in Schizophrenia", 40(9) Psych. News 29 (2005).

Bai, et al., "Therapeutic Effect of of Pirenzepine for Clozapine-Induced Hypersalivation: A Randomized, Double-Blind, Placebo Controlled, Cross-Over Study", J. Clin. Psychopharmacol., 21(6):608-11 , (2001).

(Continued)

*Primary Examiner* — Anna R Falkowitz

(74) *Attorney, Agent, or Firm* — Dennis A. Bennett; Clifford A. Schlecht; Global Patent Group, LLC

(57) ABSTRACT

The present disclosure provides a method of treating a central nervous system disorder in a patient in need thereof. The method comprises orally administering between 75 mg and 300 mg xanomeline and between 20 mg and 200 mg trospium chloride to the patient during a 24-hour period. The central nervous system disorder is selected from schizophrenia, Alzheimer's disease, Huntington's disease, Parkinson's disease, and Lewy Body dementia, wherein use of the trospium chloride alleviates a side effect associated with use of the xanomeline.

16 Claims, 1 Drawing Sheet

(56) References Cited

U.S. PATENT DOCUMENTS

| | | | |
|---|---|---|---|
| 7,786,166 B2 | 8/2010 | Frey, II | |
| 7,790,905 B2 | 9/2010 | Tawa | |
| 8,404,701 B2 | 3/2013 | Chase | |
| 9,561,218 B2 | 2/2017 | Clarence-Smith | |
| 10,238,643 B2 | 3/2019 | Elenko | |
| 10,265,311 B2 | 4/2019 | Elenko | |
| 2002/0010216 A1* | 1/2002 | Rogosky | A61K 31/137 514/649 |
| 2003/0068365 A1 | 4/2003 | Suvanprakorn | |
| 2004/0023951 A1 | 2/2004 | Bymaster | |
| 2004/0058914 A1* | 3/2004 | Doi | A61K 31/221 514/220 |
| 2004/0224012 A1 | 11/2004 | Suvanprakorn | |
| 2005/0085463 A1 | 4/2005 | Weiner | |
| 2005/0250767 A1 | 11/2005 | Weiner | |
| 2005/0267078 A1 | 12/2005 | Gras Escardo | |
| 2006/0189651 A1 | 8/2006 | Gras Escardo | |
| 2006/0197831 A1 | 9/2006 | Takeuchi | |
| 2006/0287294 A1 | 12/2006 | Zhu | |
| 2007/0027160 A1 | 2/2007 | Asselin | |
| 2007/0049576 A1* | 3/2007 | Barlow | A61K 31/00 514/214.03 |
| 2007/0053995 A1 | 3/2007 | Paborji | |
| 2007/0116729 A1 | 5/2007 | Palepu | |
| 2008/0045565 A1 | 2/2008 | Gras Escardo | |
| 2008/0114014 A1 | 5/2008 | Rich | |
| 2009/0005722 A1 | 1/2009 | Jennlngs-Spring | |
| 2009/0275629 A1 | 11/2009 | Paborji | |
| 2009/0318522 A1 | 12/2009 | Paborji | |
| 2010/0137392 A1 | 6/2010 | Paborji | |
| 2010/0152263 A1 | 6/2010 | Paborji | |
| 2010/0226943 A1 | 9/2010 | Brennan | |
| 2017/0095465 A1 | 4/2017 | Elenko | |

FOREIGN PATENT DOCUMENTS

| | | |
|---|---|---|
| EP | 0813870 A1 | 12/1997 |
| EP | 2002843 | 12/2008 |
| EP | 2002844 | 12/2008 |
| JP | H10059848 | 3/1998 |
| JP | 2000516213 | 12/2000 |
| JP | 2004502655 | 1/2004 |
| JP | 2005530742 | 10/2005 |
| JP | 20050530742 | 10/2005 |
| JP | 2007510656 | 4/2007 |
| JP | 2009507021 | 2/2009 |
| WO | 1998005207 | 2/1998 |
| WO | 1998005208 | 2/1998 |
| WO | 1998005291 | 2/1998 |
| WO | 1998005324 | 2/1998 |
| WO | 1998005325 | 2/1998 |
| WO | 1998005326 | 2/1998 |
| WO | 1998030243 | 7/1998 |
| WO | 2003030818 | 4/2003 |
| WO | 2003092580 | 11/2003 |
| WO | 2003092580 A2 | 11/2003 |
| WO | 2004060347 | 7/2004 |
| WO | 2004087161 | 10/2004 |
| WO | 2006067494 | 6/2006 |
| WO | 2006067496 | 6/2006 |
| WO | 2006086698 | 8/2006 |
| WO | 2007027675 | 3/2007 |
| WO | 2007049098 | 5/2007 |
| WO | 2008076287 | 7/2007 |
| WO | 2007125287 | 11/2007 |
| WO | 2007125290 | 11/2007 |
| WO | 2007125293 | 11/2007 |
| WO | 2007127196 | 11/2007 |
| WO | 2007128674 | 11/2007 |
| WO | 2008096111 | 8/2008 |
| WO | 2008096121 | 8/2008 |
| WO | 2008096126 | 8/2008 |
| WO | 2008096136 | 8/2008 |
| WO | 2008103351 | 8/2008 |
| WO | 2008104776 | 9/2008 |
| WO | 2008121268 | 10/2008 |
| WO | 2009036243 | 3/2009 |
| WO | 2009037503 | 3/2009 |
| WO | 2009039460 | 3/2009 |
| WO | 2009092601 | 7/2009 |
| WO | 2009132239 | 10/2009 |
| WO | 2010024870 | 3/2010 |
| WO | 2010064047 | 6/2010 |
| WO | 2010102218 | 9/2010 |
| WO | 2011011060 | 1/2011 |
| WO | 2011085406 | 7/2011 |
| WO | 2011123836 | 10/2011 |
| WO | 2012033956 | 3/2012 |
| WO | 2012170676 | 12/2012 |
| WO | 2016144727 | 9/2016 |
| WO | 2016144749 | 9/2016 |
| WO | 2017044714 | 3/2017 |
| WO | 2017127073 | 7/2017 |
| WO | 2017147104 | 8/2017 |

OTHER PUBLICATIONS

Barak, S. et al., "The M1/M4 preferring agonist xanomeline reverses amphetamine-, MK801- and scopolamine-induced abnormalities of latent inhibition: putative efficacy against positive, negative and cognitive symptoms in schizophrenia", Int J of Neuropschyopharm, 14:1233-46, (2011).

Bender, et al., "Classics in Chemical Neuroscience: Xanomeline", ACS Chem. Neurosci., 8(3):435-43, (2017).

Bewley, et al., "Discovery of a Novel, CNS Penetrant M4 PAM Chemotype Based on a 6+-Fluoro-4-(piperidin-1-yl)quinolone-3-Carbonite Core", 27 Bioorg. & Med. Chem. Lett. 4274-9, (2017).

Bodick, et al., "Effects of Xanomeline, a Selective Muscarinic Receptor Agonist, on Cognitive Function and Behavioral Symptoms in Alzheimer Disease", 54 Arch. Neurol. 465-73, (1997).

Bonifazi, et al., "Synthesis and Biological Evaluation of a Novel Series of Heterobivalent Muscarinic Ligands Based on Xanomeline and 1-[3-(4-Butylpiperin-1-yl)propyl]-1,2,3,4-Tetrahydroquinolin-2-one (77-LH-28-1)", 57 J. Med. Chem., 9065-77, (2014).

Bradley, et al., "AC-260584, An Orally Bioavailable M1 Muscarinic Receptor Allosteric Agonist Improves Cognitive Performance in an Animal Model", 58 Neuropharmacol., 365-73, (2010).

Brown, et al., "Causes of the Excess Mortality of Schizophrenia", 177 Br. J. Psych. 212-7, (2000).

Bymaster & Felder, "Role of the Cholinergic Muscarinic System in Bipolar Disorder and Related Mechanism of Action of Antipsychotic Agents", 7(Suppl. 1) Mol. Psych. S57-S63, (2000).

Bymaster, F. et al., "Neurochemical Effects of the M1 Muscarinic Agonist Xanomeline (LY246708/NNC11-0232)", JPET, 269(1):282-9, (1994).

Bymaster, F. et al., "Xanomeline compared to other muscarinic agents on stimulation of phosphoinositide hydrolysis in vivo and other cholinomimetic effects", Brain Res., 795:179-90, (1998).

Carey, et al., "SCH 57790, A Selective Muscarinic M2 Receptor Antagonist, Releases Acetylcholine and Produces Cognitive Enhancement in Laboratory Animals", 431 Eur. J. Pharmacol. 189-200, (2001).

Carnicella, S. et al., "Cholinergic effects on fear conditioning II: nicotinic and muscarinic modulations of atropine-induced disruption of the degraded contingency effect", Psychopharmacology, 178:533-41, (2005).

Caulfield & Birdsall, "International Union of Pharmacology. XVII. Classification of Muscarinic Acetylcholine Receptors", Pharmacol. Rev., 50(2):279-90, (1998).

Coward, "General Pharmacology of Clozapine", Br. J. Psych., 160(Suppl. 17): 5-11, (1992).

Croissant et al., "Reduction of Side Effects by Combining Clozapine with Amisulpride: Case Report and Short Review of Clozapine-Induced Hypersalivation", 38 Pharmacopsych. 38-39, (2005).

Cutler & Sramek, "Scientific and Ethical Concerns in Clinical Trials in Alzheimers Patients: The Bridging Study", 48 Eur. J. Clin. Pharmacol. 421-8, (1995).

(56) References Cited

OTHER PUBLICATIONS

Davydov & Botts, "Clozapine-Induced Hypersalivation", 34 Ann. Pharmacother. 662-5, (2000).
Dawe, et al., "Pathophysiology and Animal Models of Schizophrenia", Ann. Acad. Med. Singapore, 38(5):425-30, (2009).
Dean, et al., "The Density of Muscarinic M1 Receptors is Decreased in the Caudate-Putamen of Subjects with Schizophrenia", 1 Mol. Psych. 54-8, (1996).
Desbonnet et al., "Mutant Models for Genes Associated with Schizophenia", 37(part 1) Biochem. Soc. Trans. 308-12, (2009).
Dixit & Puthli, "Oral Strip Technology: Overview and Future Potential", 139 J. Control. Release 94-107, (2009).
Eglen, "Muscarinic Receptor Subtypes in Neuronal and Non-Neuronal Cholinergic Function", 26 Auton. Auta. Pharmacol. 219-33, (2006).
Ellis, et al., "Muscarinic and Nicotinic Receptors Synergistically Modulate Working Memory and Attention in Humans", 9 Int. J. Neuropsychopharmacol., 175-89, (2006).
Fogueri & Singh, "Smart Polymers for Controlled Delivery of Proteins and Peptides: A Review of Patents", 3 Recent Pat. Drug Deliv. Formul. 40-8, (2009).
Geyer, "Developing Translational Animal Models for Symptoms of Schizophrenia or Bipolar Manina", 14(1) Neurotox. Res. 71-8, (2008).
Gralewicz, et al., "Interaction of Chlorphenvinphos with Cholinergic Receptors in the Rabbit Hypothalamus", 17(3) Neurotoxicol. Teratol. 289-95, (1995).
Iconomopoulou, et al., "Incorporation of Small Molecular Weight Active Agents into Polymeric Components", 2 Recent Pat. Drug Deliv. Formul. 94-107, (2008).
International Application No. PCT/US2010/002044; International Preliminary Report on Patentability, dated Jan. 24, 2012; 5 pages.
International Application No. PCT/US2010/002044; International Search Report and Written Opinion of the International Search Authority, dated Sep. 2, 2010; 6 pages.
Iwanaga, et al., "Carbachol Induces Ca2+-Dependent Contraction via Muscarinic M2 and M3 Receptors in Rat Intestinal Subepithelial Myofibroblasts", 110 J. Pharmacol. Sci. 306-14, (2009).
Jones, et al., "Novel Selective Allosteric Activator of the M1 Muscarinic Acetylcholine Receptor Regulates Amyloid Processing and Produces Antipsychotic-Like Activity in Rats", J. Neurosci., 28(41):10422-33, (2008).
Kahl, et al., "Therapie der Clozapin-Induzierten Hypersalivations Mit Botulinum-Toxin B", 76 Nervenarzt, 205-8, (2005).
Kalantzi, et al., "Recent Advances in Oral Pulsatile Drug Delivery", 3 Recent Pat. Drug Deliv. Formul. 49-63, (2009).
Kreinin, et al., "Sulpiride Addition for the Treatment of Clozapine-Induced Hypersalivation: Preliminary Study", Isr. J. Pysch. Relat. Sci., 42(1):61-3, (2005).
Kurimoto, et al., "An Approach to Discovering Novel Muscarinic M1 Receptor Positive Allosteric Modulators with Potent Cognitive Improvement and Minimized Gastrointestinal Dysfunction", J. Pharmacol. Exp. Ther. doi: 10.1124/jpet.117.243774. [Epub ahead of print] (2017).
Langmead, et al., "Muscarinic Acetylcholine Receptors as CNS Drug Targets", 117 Pharmacol. Ther., 232-43, (2008).
Li, et al., "Xanomeline Derivative EUK1001 Attenuates Alzheimer's Disease Pathology in Triple Transgenic Mouse Model", 16 Mol. Med. Rept. 7835-40, (2017).
Li, Z. et al., "Effect of muscarinic receptor agonists xanomeline and sabcomeline on acetylcholine and dopamine efflux in the rat brain; comparison with effects of 4-[3-(4-butylpiperidin-1-yl)-propyl]-7 fluoro-4H-benzo[1,4]oxazin-3-one (AC260584) and N-desmethylclozapine", European J of Pharmacology, 596:89-97, (2008).
Liu, et al., "Design and Synthesis of N-[6-(Substituted Aminoethylideneamino)-2-Hydroxyindan-1-yl]arylamides as Selective and Potent Muscarinic M1 Agaonists", 25 Bioorg. & Med. Chem. Lett., 4153-63, (2015).
Long, et al., "Discovery of a Novel 2,4-Dimethylquinoline-6-Carboxmide M4 Positive Allosteric Modulator (PAM) Chemotype via Scaffold Hopping", 27 Bioorg. Med. Chem. Lett., 4999-5001, (2017).
Luo, et al., "CHRM2 Gene Predisposes to Alcohol Dependence, Drug Dependence and Affective Disorders: Results From an Extended Case-Control Structured Association Study", Hum. Mol. Genet., 14(16):2421-34, (2005).
Material Safety Data Sheet—Lethal Nerve Agent Sarin, Appendix to the Riegle Report: US Chemical and Biological Warfare-Related Dual Use Exports to Iraq and Their Possible Impact on the Health Consequences of the Gulf War, U.S. Senate, 103d Congress, 2d Session, May 25, 1994, available at www.gulfweb.org/bigdoc/report/appbg/html (last visited Jun. 4, 2015).
Medina, et al., "Effects of Central Muscarinic-1 Receptor Stimulation on Blood Pressure Regulation", Hypertension, 29(3):828-34, (1997).
Messer Jr., et al., "Design and Development of Selective Muscarinic Agonists for the Treatment of Alzheimer's Disease: Characterization of Tetrahydropyrimidine Derivatives and Development of New Approaches for Improved Affinity and Selectivity for M1 Receptors", 74 Pharmaceutica Acta Helvetiae, 135-40, (2000).
Mizrahi & Domb, "Mucoadhesive Polymers for Delivery of Drugs to the Oral Cavity", 2 Recent Pat. Drug Deliv. Formul. 108-19, (2008).
Mobascher, et al., "Association of a Variant in the Muscarinic Acetylcholine Receptor 2 Gene (CHRM2) with Nicotine Addiction", 153B Am. J. Med. Genet. Part B 684-90, (2010).
Mortimer, et al., "Syptoms Rating Scales and Outcome in Schizophrenia", Br. J. Pysch., 191(Suppl. 50):s7-14, (2007).
Mouradian, et al., "No Response to High-Dose Muscarinic Agonist Therapy in Alzheimer's Disease", 38 Neurol. 606-8, (1988).
Nikam & Awasthi, "Evolution of Schizophrenia Drugs: A Focus on Dopaminergic Systems", Curr. Opin. Investig. Drugs, 9(1):37-46, (2008).
Panos, et al., "New Drug Delivery Systems Based on Chitosan", 5 Curr. Drug Discov. Technol. 333-41, (2008).
Praharaj, et al., "Is Clonidine Useful for Treatment of Clozpine-Induced Sialorrhea?", J. Psychopharmacol., 19(5):426-8, (2005).
Raedler, et al., "In Vivo Determination of Muscarinic Acetylcholine Receptor Availability in Schizophrenia", 160 Am. J. Psych. 118-27, (2003).
Rogers & Shramko, "Therapeutic Options in the Treatment of Clozapine-Induced Sialorrhea", Pharmacother., 20(9):1092-5, (2000).
Schneider, et al., "Reduction of Clozapine-Induced Hypersalivation by Pirenzepine is Safe", 37 Pharmacopsych., 43-5, (2004).
Schultz, et al., "Schizophrenia: A Review", Am. Fam. Physician, 75(12):1821-9, (2007).
Shannon, H. et al., "Xanomeline, anM1/M4 preferring muscarinic cholinergic receptor agonist, produces antipsychotic-like activity in rats and mice", Schizophrenia Res., 42:249-59, (2000).
Shekhar, et al., "Selective Muscarinic Receptor Agonist Xanomeline as a Novel Treatment Approach for Schizophrenia", Am. J. Psych., 165(8):1033-9, (2008).
Shirey, et al., "An Allosteric Potentiator of M4 mAChR Modulates Hippocampal Synaptic Transmission", Nature Chem. Biol., 4(1):42-50, (2008).
Si, et al., "A Novel Derivative of Xanomeline Improves Fear Cognition in Aged Mice", 473 Neurosci. Lett., 115-9, (2010).
Sramek, et al., "The Safety and Tolerance of Xenomeline Tartrate in Patients with Alzheimer's Disease", 35 J. Clin, Pharmacol., 800-6, (1995).
Supplementary European Search Report, EP10802549, dated Sep. 30, 2013.
Syed, et al., "Pharmacological Inventions for Clozapine-Induced Hypersalivation", 3 Cochrane Database Sys. Rev. 1-62, (2008).
Tarr, et al., "Challenges in the Development of an M4 PAM Preclinical Candidate: The Discovery, SAR, and In Vivo Characterization of a Series of 3-Aminoazetidine-Derived Amides", 27 Bioorg. & Med. Chem. Lett., 2990-5, (2017).
U.S. Appl. No. 14/534,698; Non-Final Office Action dated Nov. 24, 2015; 11 pages.

(56) References Cited

OTHER PUBLICATIONS

U.S. Appl. No. 15/378,796; Applicant Initiated Interview Summary dated Jul. 30, 2018, 3 pages.
U.S. Appl. No. 15/378,796; Applicant Initiated Interview Summary dated Jun. 12, 2018; 4 pages.
U.S. Appl. No. 15/378,796; Final Office Action dated Jan. 4, 2018; 14 pages.
U.S. Appl. No. 15/378,796; Non-Final Office Action dated May 24, 2017; 11 pages.
U.S. Appl. No. 15/400,108; Applicant Initiated Interview Summary dated Jun. 12, 2018; 3 pages.
U.S. Appl. No. 15/400,108; Applicant-Initiated Interview Summary, dated Oct. 12, 2018; 3 pages.
U.S. Appl. No. 15/400,108; Final Office Action dated Jul. 18, 2017; 14 pages.
U.S. Appl. No. 15/400,108; Non-Final Office Action dated Feb. 24, 2017; 11 pages.
U.S. Appl. No. 15/400,108; Non-Final Office Action dated Sep. 7, 2018; 43 pages.
U.S. Appl. No. 15/400,108; Notice of Allowance, dated Nov. 8, 2018; 23 pages.
U.S. Appl. No. 15/400,108; Notice of Appeal dated Jan. 17, 2018; 1 page.
U.S. Appl. No. 15/738,796; Applicant-Initiated Interview Summary dated Mar. 4, 2019; 3 pages.
U.S. Appl. No. 15/738,796; Notice of Allowance dated Sep. 6, 2018; 15 pages.
U.S. Appl. No. 16/270,206; Application as filed dated Feb. 7, 2017; 57 pages.
Vardigan, et al., "Improved Cognition Without Adverse Effects: Novel M1 Muscarinic Potentiator Compares Favorably to Donepezil and Xanomeline in Rhesus Monkey", 232 Psychopharmacol., 1859-66, (2015).
Wan, et al., "Use of Degradable and Nondegradable Nanomaterials for Controlled Release", Nanomed., 2(4):483-509, (2007).
Witte, et al., "Muscarinic Receptor Antoagonists for Overactive Bladder Treatment: Does One Fit All?", 19 Curr. Opin. Urol., 13-9, (2009).
Wood, et al., "Discovery of VU0467485/AZ13713945: An M4 PAM Evaluated as a Preclinical Candidate for the Treatment of Schizophrenia", 8 ACS Med. Chem. Lett., 233-8, (2017).
U.S. Appl. No. 16/270,206; Applicant-Initiated Interview Summary, dated May 9, 2019; 7 pages.
U.S. Appl. No. 16/270,206; Applicant-Initiated Interview Summary, dated May 24, 2019; 3 pages.
U.S. Appl. No. 16/270,206; Non-Final Office Action, dated Apr. 16, 2019; 28 pages.
U.S. Appl. No. 15/738,796; Applicant-Initiated Interview Summary, dated Apr. 2, 2019; 3 pages.

\* cited by examiner

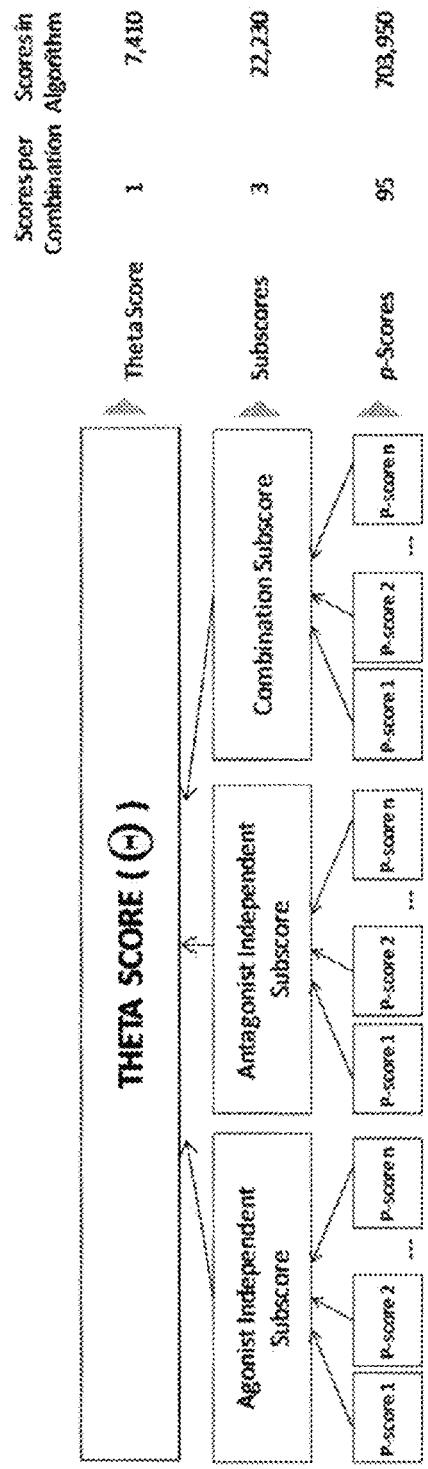

METHODS AND COMPOSITIONS FOR TREATMENT OF DISORDERS AMELIORATED BY MUSCARINIC RECEPTOR ACTIVATION

This application claims the benefit of the filing date as a continuation of application Ser. No. 15/400,108, filed on Jan. 6, 2017, now allowed, which is continuation of application Ser. No. 15/161,840, filed on May 23, 2016, now abandoned, which is a continuation of application Ser. No. 14/534,698, filed on Nov. 6, 2014, now abandoned, which is a continuation of application Ser. No. 13/858,985, filed on Apr. 9, 2013, now abandoned, which is continuation of application Ser. No. 13/592,480, filed on Aug. 23, 2012, now abandoned, which is a continuation of application Ser. No. 13/348,057, filed on Jan. 11, 2012, now abandoned, which is a continuation of application Ser. No. 12/840,980, filed on Jul. 21, 2010, now abandoned, which is a non-provisional of U.S. Provisional Patent Application Ser. No. 61/213,853, filed Jul. 22, 2009, and a non-provisional of U.S. Provisional Patent Application Ser. No. 61/282,658 filed Mar. 15, 2010, the disclosures of which are each incorporated by reference in their entireties for all purposes.

The present invention relates to: I) A method of using a combination of one or more muscarinic agonists and one or more muscarinic antagonists for treatment of diseases that are ameliorated by activation of muscarinic receptors (e.g., schizophrenia and related disorders); 2) A medicament comprising one or more muscarinic agonists and one or more muscarinic antagonists.

The acetylcholine neurotransmitter system plays a significant role in a variety of central nervous system (CNS) and peripheral functions. Acetylcholine signaling occurs through two different families of receptors: nicotinic receptors and muscarinic receptors. Muscarinic cholinergic receptors are G-protein coupled receptors with five different receptor subtypes (M1-M5) (Raedler et al. *American Journal of Psychiatry.* 160: 118. 2003), each of which are found in the CNS but have different tissue distributions. Activation of the muscarinic system through use of muscarinic agonists has been suggested to have the potential to treat several diseases including Alzheimer's disease, Parkinson's disease, movement disorders and drug addiction. (US 2005/0085463; Langmead et al. *Pharmacology & Experimental Therapeutics.* 117: 232:2008). Genetic evidence has suggested a direct link between the muscarinic system and both alcohol addiction (Luo X. Et al. *Hum Mal Genet.* 14:2421. 2005) and nicotine addiction (Mobascher A et al. *Am J Med Genet B Neuropsychiatr Genet.* 5:684. 2010). M1 and M4 subtypes have been of particular interest as therapeutic targets for various diseases. For instance, the mood stabilizers lithium and valproic acid, which are used to treat bipolar depression, may exert their effects via the muscarinic system particularly through the M4 subtype receptor. (Bymaster & Felder. *Mal Psychiatry.* 7 Suppl I:S57. 2002).

Some of the strongest linkages to the muscarinic system have been with schizophrenia, which is a serious mental illness affecting approximately 0.5-1% of the population. (Arehart-Treichel. *Psych News.* 40:9. 2005). The disease is characterized by a set of symptoms that are generally divided into three categories: 1) Positive symptoms (e.g., hallucinations, delusional thoughts, etc.); 2) Negative symptoms (e.g., social isolation, anhedonia, etc.); and 3) Cognitive symptoms (e.g., inability to process information, poor working memory, etc.). (Schultz. *Am Fam Physician.* 75:1821. 2007). Patients who suffer from schizophrenia both experience a major decline in quality of life and are at increased risk for mortality due to a number of factors, such as an increased suicide rate. (Brown et al. *British Journal of Psychiatry.* 177: 212. 2000). The cost of schizophrenia to society is also significant as sufferers of schizophrenia are much more likely to be incarcerated, homeless or unemployed.

Today, antipsychotics are the mainstay of treatment for schizophrenia. The first generation of antipsychotics are generally known as "typical antipsychotics" while newer antipsychotics are generally called "atypical antipsychotics." Both typical and atypical antipsychotics have limited efficacy and severe side effects. There is little to no difference in efficacy between typical and atypical antipsychotics, most likely due to the fact that both classes of drugs achieve their therapeutic effect through the same pharmacological mechanisms (e.g., acting as dopamine receptor antagonists). (Nikam et al. *Curr Opin Investig Drugs.* 9:37. 2008). Side effects of typical antipsychotics include abnormal movement (e.g., rigidity) whereas atypicals have different but equally significant side effects (e.g., major weight gain, cardiovascular effects, etc.). The side effect profile of current antipsychotics further decreases compliance in a patient population that is already frequently non-compliant. Thus, there exists a clear need for new therapeutics to treat schizophrenia and related disorders (e.g., schizoaffective disorder).

Clozapine is an example of an antipsychotic that has major side effects, including sialorrhea (hypersalivation) which occurs in up to 54% of patients. (Davydov and Botts, *Ann Pharmacother.* 34:662. 2000). The exact mechanism of hypersalivation remains unknown. (Rogers and Shramko. *Pharmacotherapy.* 20:109. 2000). Clozapine has a complex pharmacological profile with appreciable activity at a variety of receptors, including dopamine receptors, serotonin receptors, adrenergic receptors, muscarinic receptors and possibly others. (Coward. *Br J Psychiatry Suppl.* 17:5. 1992). Investigators have tried a variety of pharmacological approaches in an attempt to counteract sialorrhea, including botulinum toxin (Kahl et al. *Nervenarzt.* 76:205. 2005) as well as the antipsychotics amisulpride (Croissant et al. *Pharmacopsychiatry.* 38:38. 2005) and sulpiride. (Kreinin et al. *Isr J Psychiatry Relat Sci.* 42:61. 2005). Efforts have focused mostly on alpha2 adrenergic agonists as well as anti-cholinergic drugs due to clozapine's known interaction with these receptors. Anti-muscarinic drugs such as pirenzepine have shown efficacy in small scale trials (Schneider et al. *Pharmacopsychiatry.* 37:43. 2004), but other trials with the same agent found no effect. (Bai et al. *J Clin Psychopharmacol.* 21:608. 2001). Alpha2 adrenergic agonist such as clonidine (Singh et al., *J Psychopharmacol.* 19:426. 2005) have also shown efficacy in reducing sialorrhea in small scale trials. However, Syed et al. reported in a 2008 review that there is inadequate data to guide clinical practice. (Syed et al. *Cochrane Database Syst Rev.* 16:3. 2008).

Another approach to the treatment of schizophrenia has been use of muscarinic agonists. Muscarinic receptors are G-protein linked receptors that bind the neurotransmitter acetylcholine. (Eglen R M. *Auton Autacoid Pharmacol* 26: 219. 2006). To date, five subtypes of muscarinic receptor have been identified and are generally labeled M1, M2, M3, M4, and MS, respectively. (Caulfield M P et al. *Pharmacol. Rev.* 50: 279. 1998). These muscarinic subtypes vary in terms of the affinity of various agonists and antagonists for the receptors. A number of lines of evidence have suggested that the muscarinic system plays a significant role in the pathology of schizophrenia. In particular, decreased expression of M1 and M4 receptor subtypes has been noted in post-mortem studies in deceased schizophrenic patients. (Dean et al. *Mal Psych.* I: 54. 1996). Likewise, SPECT imaging studies have shown decreased muscarinic availability in schizophrenia. (Raedler et al. *Am J Psych.* 160:118. 2003).

There is also pharmacological evidence implicating activation of muscarinic receptors as a potential therapeutic approach to schizophrenia. For example, the muscarinic antagonist scopolamine, which is used to treat motion sickness, produces cognitive impairment and delusions of the type seen in schizophrenia. (Ellis et al. *Int. J Neuropsychopharmacol.* 9:175. 2006). More selective M1 agonists have been suggested to potentiate glutamate signaling which could help exert a therapeutic effect. (Jones et al. *J Neurosci.* 28:10422. 2008). In a double-blind placebo-controlled trial of schizophrenic patients using xanomeline, which has preferential activity at the M1 and M4 receptors, alleviation of schizophrenia was observed. (Shekhar et al. *Am. J Psych.* 165: 1033. 2008). However, because xanomeline also bound to subtypes of receptors other than M1, a number of various serious side effects were observed including GI side effects, cardiac side effects and problems with hyper-salivation.

To date, nobody has been able to harness the approach of employing muscarinic agonists because of the side effects associated with the agents' binding certain muscarinic receptor subtypes. A need exists for a method of using muscarinic agonists and for a medicament employing such muscarinic agonists that would allow for the therapeutic effects associated with activation of muscarinic receptors, but with fewer side effects.

SUMMARY OF THE INVENTION

In one embodiment, the present invention relates to a method of treating diseases or conditions ameliorated by activation of the muscarinic system by administering one or more muscarinic "Activators" (e.g., agonist, partial agonist, co-agonist, physiological agonist, potentiator, stimulator, allosteric potentiator, positive allosteric modulator or allosteric agonist) and one or more muscarinic "Inhibitors" (e.g., antagonist, partial antagonist, competitive antagonist, non-competitive antagonist, uncompetitive antagonist, silent antagonist, inverse agonist, reversible antagonist, physiological antagonist, irreversible antagonist, inhibitor, reversible inhibitor, irreversible inhibitor, negative allosteric modulator, or allosteric antagonist). In a preferred embodiment, such diseases include schizophrenia and related disorders. In a preferred embodiment, a single muscarinic Activator and a single muscarinic Inhibitor are used. In a preferred embodiment, the combination of the Activator and Inhibitor has a score ("Theta score") above 230 as determined by in silico testing using a proprietary algorithm as described herein. In another embodiment, more than one muscarinic Activator and/or more than one muscarinic Inhibitor are used.

In another embodiment of the invention, the method of treatment can be applied to a mammal. In another embodiment, the mammal is a human being.

In one embodiment of the invention, the use of the Inhibitor alleviates the side effects associated with use of the Activator. In another embodiment, use of the Inhibitor allows for a higher maximum tolerated dose of the Activator.

In one embodiment, the muscarinic Activator may be taken sequentially with the Inhibitor. In another embodiment of the invention, the muscarinic Activator may be taken concurrently with the Inhibitor. In a preferred embodiment of the invention, the Activator and Inhibitor are formulated to be contained in the same dosage form or dosage vehicle. In another embodiment of the invention, the muscarinic Activator and Inhibitor are formulated to be in separate dosage forms or dosage vehicles. In one embodiment, the Activator and Inhibitor are formulated in an immediate release dosage form. In another embodiment, Activator and Inhibitor are formulated in a controlled release dosage form. In another embodiment, either the Activator or the Inhibitor is formulated in an immediate release dosage form, while the other is formulated in a controlled release dosage form.

In another embodiment of the invention, the muscarinic Activator and Inhibitor can be taken orally. The Activator and Inhibitor may be given orally in tablets, troches, liquids, drops, capsules, caplets and gel caps or other such formulations known to one skilled in the art. Other routes of administration can include but are not limited to: parenteral, topical, transdermal, ocular, rectal, sublingual, and vaginal.

In another embodiment of the invention, the muscarinic Activator and Inhibitor are administered either simultaneously or consecutively with other therapies for schizophrenia. In one embodiment of the invention, the muscarinic Activator and Inhibitor are used simultaneously or sequentially with psychotherapy. In another embodiment of the invention, the muscarinic Activator and Inhibitor are administered either simultaneously or consecutively with other pharmacological therapies. Pharmacological therapies could include but are not limited to: antipsychotics, anxiolytics, anti-depressants, sedatives, tranquilizers and other pharmacological interventions known to one skilled in the art.

A separate embodiment of the invention is a medicament comprising both a muscarinic Activator and a muscarinic Inhibitor. In a preferred embodiment, the combination of the Activator and Inhibitor have a theta score above 230 as determined by in silico testing using a proprietary algorithm as described herein.

In another embodiment of the invention, the medicament can be taken orally. The medicament may be given orally in tablets, troches, liquids, drops, capsules, caplets and gel caps or other such formulations known to one skilled in the art. Other routes of administration can include but are not limited to: parenteral, topical, transdermal, ocular, rectal, sublingual, and vaginal.

In another embodiment of the invention, the medicament can be administered in conjunction with other therapies. In one embodiment of the invention, the medicament is used simultaneously or sequentially with psychotherapy. In another embodiment of the invention, the medicament is administered either simultaneously or consecutively with other pharmacological therapy. Such pharmacological therapy could include but is not limited to: antipsychotics, anxiolytics, anti-depressants, sedatives, tranquilizers and other pharmacological interventions known to one skilled in the art.

These and other embodiments of the invention, and their features and characteristics, will be described in further detail in the description and claims that follow.

BRIEF DESCRIPTION OF THE DRAWING

FIG. 1 illustrates the relationships among p-Scores, Sub-scores, and Theta Scores in accordance with the present invention.

DETAILED DESCRIPTION

Definitions

For convenience, before further description of the present invention, certain terms employed in the specification, examples and appended claims are collected here. These definitions should be read in light of the remainder of the disclosure and understood as by a person of skill in the art. Unless defined otherwise, all technical and scientific terms used herein have the same meaning as would be understood by a person of ordinary skill in the art.

The articles "a" and "an" are used herein to refer to one or to more than one (i.e. to at least one) of the grammatical object of the article. By way of example, "an element" means one element or more than one element.

The terms "comprise" and "comprising" are used in the inclusive, open sense, meaning that additional elements may be included.

The term "consisting" is used to limit the elements to those specified except for impurities ordinarily associated therewith.

The term "consisting essentially of" is used to limit the elements to those specified and those that do not materially affect the basic and novel characteristics of the material or steps.

As used herein, unless otherwise specified, the term "controlled release" is defined as a prolonged release pattern of one or more drugs, such that the drugs are released over a period of time. A controlled release formulation is a formulation with release kinetics that result in measurable serum levels of the drug over a period of time longer than what would be possible following intravenous injection or following administration of an immediate release oral dosage form. Controlled release, slow release, sustained release, extended release, prolonged release, and delayed release have the same definitions for the present invention.

The term "including" is used herein to mean "including but not limited to." "Including" and "including but not limited to" are used interchangeably.

The term "mammal" is known in the art, and exemplary mammals include humans, primates, bovines, porcines, canines, felines, and rodents (e.g., mice and rats).

The terms "parenteral administration" and "administered parenterally" are art-recognized and refer to modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intra-articular, subcapsular, subarachnoid, intraspinal, and intrasternal injection and infusion.

A "patient," "subject" or "host" to be treated by the subject method may mean either a human or non-human mammal.

The term "pharmaceutically-acceptable carrier" is art-recognized and refers to a pharmaceutically-acceptable material, composition or vehicle, such as a liquid or solid filler, diluent, excipient, solvent or encapsulating material, involved in carrying or transporting any subject composition or component thereof from one organ, or portion of the body, to another organ, or portion of the body. Each carrier must be "acceptable" in the sense of being compatible with the subject composition and its components and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

The term "pharmaceutically-acceptable salts," used interchangeably with "salts," is art-recognized and refers to salts prepared from relatively non-toxic acids or bases including inorganic acids and bases and organic acids and bases, including, for example, those contained in compositions of the present invention. Suitable non-toxic acids include inorganic and organic acids such as acetic, benzenesulfonic, benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic, hydrochloric, hydrobromic, phosphoric, and sulfuric acids and the like.

The term "treating" is art-recognized and refers to curing as well as ameliorating at least one symptom of any condition or disorder.

The term "therapeutic agent" is art-recognized and refers to any chemical moiety that is a biologically, physiologically, or pharmacologically active substance that acts locally or systemically in a subject. Examples of therapeutic agents, also referred to as "drugs," are described in well-known literature references such as the Merck Index ($14^{th}$ edition), the Physicians' Desk Reference ($64^{th}$ edition), and The Pharmacological Basis of Therapeutics ($12^{th}$ edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment.

The term "psychotherapy" refers to use of non-pharmacological therapies in which those skilled in the art use a variety of techniques that involve verbal and other interactions with a patient to affect a positive therapeutic outcome. Such techniques include, but are not limited to, behavior therapy, cognitive therapy, psychodynamic therapy, psychoanalytic therapy, group therapy, family counseling, art therapy, music therapy, vocational therapy, humanistic therapy, existential therapy, transpersonal therapy, client-centered therapy (also called person-centered therapy), Gestalt therapy, biofeedback therapy, rational emotive behavioral therapy, reality therapy, response based therapy, Sandplay therapy, status dynamics therapy, hypnosis and validation therapy. It is further understood that psychotherapy may involve combining two or more techniques and that a therapist can select and adjust the techniques based on the needs of the individual patient and the patient's response.

The term "Muscarinic Disorder" refers to any disease or condition that is ameliorated by activation of the muscarinic system. Such diseases include ones in which direct activation of muscarinic receptors themselves or inhibition of cholinesterase enzymes has produced a therapeutic effect.

The terms "Diseases Related To Schizophrenia" and "Disorders Related To Schizophrenia" include, but are not limited to, schizo-affective disorder, psychosis, delusional disorders, psychosis associated with Alzheimer's disease, psychosis associated with Parkinson's disease, psychotic depression, bipolar disorder, bipolar with psychosis or any other disease with psychotic features.

The term "Movement Disorders" includes, but is not limited to, Gilles de la Tourette's syndrome, Friederich's ataxia, Huntington's chorea, restless leg syndrome and other diseases or disorders whose symptoms include excessive movements, ticks and spasms.

The term "Mood Disorders" includes major depressive disorder, dysthymia, recurrent brief depression, minor depression disorder, bipolar disorder, mania and anxiety.

The term "Cognitive Disorders" refers to diseases or disorders that are marked by cognitive deficit (e.g., having abnormal working memory, problem solving abilities, etc.). Diseases include but are not limited to Alzheimer's disease, Parkinson's Disease, dementia (including, but not limited to, AIDS related dementia, vascular dementia, age-related dementia, dementia associated with Lewy bodies and idiopathic dementia), Pick's disease, confusion, cognitive deficit associated with fatigue, learning disorders, traumatic brain injury, autism, age-related cognitive decline, and Cushing's Disease, a cognitive impairment associated with auto-immune diseases.

The term "Attention Disorders" refers to diseases or conditions that are marked by having an abnormal or decreased attention span. Diseases include but are not limited to attention hyperactivity deficit disorder, attention deficit disorder, Dubowitz Syndrome, FG Syndrome, Down's Syndrome, growth delay due to insulin-like growth factor I deficiency, hepatic encephalopathy syndrome, and Strauss Syndrome.

The term "Addictive Disorders" refers to diseases or conditions marked by addiction or substance dependence as defined by the Diagnostic & Statistical Manual IV. Such disorders are characterized by physical dependence, withdrawal and tolerance to a particular substance. Such substances include but are not limited to alcohol, cocaine, amphetamines, opioids, benzodiazepines, inhalants, nicotine, barbiturates, cocaine and *cannabis*. Addictive Disorders can also encompass behaviors that a patient does in a compulsive, continual manner despite clear negative consequences. For instance, ludomania is recognized by those skilled in the art as being an addictive behavior that often has devastating consequences.

The term "Activator" means a molecule that can be described as an agonist, partial agonist, co-agonist, physiological agonist, potentiator, stimulator, allosteric potentiator, positive allosteric modulator, allosteric agonist or a molecule that increases the activity or signaling of muscarinic receptors through direct or indirect means.

The term "Inhibitor" means a molecule that can be described as an antagonist, partial antagonist, competitive antagonist, non-competitive antagonist, uncompetitive antagonist, silent antagonist, inverse agonist, reversible antagonist, physiological antagonist, irreversible antagonist, inhibitor, reversible inhibitor, irreversible inhibitor, negative allosteric modulator, allosteric antagonist or a molecule that decreases the activity or signaling of muscarinic receptors through direct or indirect means.

The term "maximum tolerated dose" means the highest dose of a drug or therapeutic that can be taken by patients without the patients' experiencing intolerable side effects. The maximum tolerated dose is typically determined empirically in clinical trials.

The term "Muscarinic receptors" refers to G-protein linked receptors that bind the neurotransmitter acetylcholine, and to date, five subtypes of muscarinic receptor have been identified. "M1" means the subtype one muscarinic receptor. "M2" means the subtype two muscarinic receptor. "M3" means the subtype three muscarinic receptor. "M4" means the subtype four muscarinic receptor. "M5" means the subtype five muscarinic receptor.

The term "Antipsychotic" refers to a drug that diminishes psychosis, hallucinations or delusions. Antipsychotics can include, but are not limited to: haloperidol, droperidol, chlorpromazine, fluphenazine, perphenazine, prochlorperazine, thioridazine, trifluoperazine, mesoridazine, periciazine, promazine, triflupromazine, levomepromazine, promethazine, pimozide, chlorprothixene, flupenthixol, thiothixene, zuclopenthixol, clozapine, olanzapine, risperidone, quetiapine, ziprasidone, amisulpride, asenapine, paliperidone, zotepine, aripiprazole, bifeprunox, and tetrabenazine.

The term "Anxiolytics" refers to drugs that reduce anxiety, fear, panic or related feelings. Such drugs include, but are not limited to: benzodiazepines (e.g., alprazolam, chlordiazepoxide, clonazepam, clorazepate, diazepam, lorazepam), buspirone, barbiturates (e.g., amobarbital, pentobarbital, secobarbital, phenobarbital) and hydroxyzine.

The term "Anti-depressants" refers to drugs that alleviate depression and related conditions (e.g., dysthymia) and include, but are not limited to: Selective serotonin-reuptake inhibitors (e.g., citalopram, escitalopram, fluoxetine, fluvoxamine, paroxetine, sertraline), serotonin-norepinephrine reuptake inhibitors (e.g., desvenlafaxine, duloxetine, milnacipram, venlafaxine), mianserin, mirtazapin, norepinephrine reuptake inhibitors (e.g., atomoxetine, mazindol, reboxetine, viloxazine), bupropion, tianeptine, agomelatine, trycyclic antidepressants (e.g., amitriptyline, clomipramine, doxepin, imipramine, trimipramine, desipramine, nortriptyline, protriptyline), monoamine oxidase inhibitors (e.g., isocarboxazid, moclobemide, phenelzine, selegiline, tranylcypromine).

The terms "Sedatives" or "tranquilizers" refer to drugs that induce somnolence, promote a feeling of being tired or desire to sleep or promote a state of unconsciousness. Such drugs include but are not limited to benzodiazepines, barbiturates (e.g., amobarbital, pentobarbital, secobarbital, phenobarbital), eszopiclone, zaleplon, zolpidem, zopiclone.

The term "Theta Score" is defined as the numerical value assigned by an in-silico algorithm described herein used to predict the overall efficacy and side effects of any given combination of a Muscarinic Activator and a Muscarinic Inhibitor.

INTRODUCTION

The present invention relates to the method of use of one or more Activators and Inhibitors of muscarinic receptors in combination for treatment of various disorders that can be ameliorated by activation of the muscarinic system. The present invention also describes a medicament comprising one or more Activators and one or more Inhibitors of muscarinic receptors. Use of muscarinic Activators has previously been hypothesized to be useful for various central nervous system related conditions. In particular, activation of the M1 and M4 receptor subtypes could prove to be of therapeutic value. However, no one has been able to advance M1 and M4 muscarinic Activators through clinical development to receive regulatory approval for CNS indications because of unacceptable side effects. For instance, while Activators of M1 and M4 muscarinic receptors have been suggested to be efficacious treatments for schizophrenia (Shekhar et al. *Am J Psychiatry.* 165:1033. 2008; Shirey et el. *Nature Chem Biol.* 4:41. 2007), the binding by those Activators to subtypes of muscarinic receptors besides M1 and M4 results in side effects which have prevented use of muscarinic Activators in the clinic. (Shekhar et al. *Am. J Psych.* 165: 1033.2008). For instance, in both phase I and subsequent trials, the muscarinic agonist xanomeline had unacceptable GI side effects as well as other side effects primarily linked to binding of muscarinic receptors besides M1 and M4. (Sramek et al. *The Journal of Clinical Pharmacology.* 35:800. 1995), (Cutler & Sramek. *Eur. J Clin. Pharmacol.* 48:421-428. 1995), (Bodick et al. *Arch Neuro* 54:465-473. 1997). By combining a muscarinic Activator with an Inhibitor, it is possible to achieve the desired therapeutic effect while diminishing or eliminating the side effects associated with unwanted subtype binding.

Muscarinic Inhibitors are used for treatment of overactive bladder and pulmonary disorders and have been suggested for treatment of other disorders. (Witte L P et al. *Curr. Opin. Ural.* I:13. 2009). Groups have outlined use of muscarinic Inhibitors with drugs in other classes to achieve a greater effect for treatment of a disease. For example, WO 2008/121268 suggests a combination for the treatment of lower urinary tract symptoms (LUTS) consisting of a beta-3 adrenergic agonist, which on its own has been investigated for the treatment of LUTS, and a muscarinic antagonist. Others have suggested combining specific muscarinic Activators or Inhibitors with other specific therapeutic agents other than muscarinic agents to further have a therapeutic effect (e.g., WO 2009/037503, WO 2009/036243, WO 2008/104776, WO 2008/096136, WO 2008/096126, WO 2008/096121, WO 2008/096111, WO 2007/127196, WO 2007/125293, EP 2002843, EP 2002844, U.S. Pat. Nos. 5,744,476, 7,524,965, US 2005/0267078, US 2006/0189651, and US 2008/0045565). US 2006/0287294 A1 outlines use of aspartyl protease inhibitors with either an M1 agonist or an M2 antagonist for treatment of various diseases, including improvement of cognitive deficit. Both M1 Activators and M2 Inhibitors themselves (Carey et al. *Eur J Pharmacol* 43 1: 198. 2001.) have been suggested to be useful treatments for cognitive deficit, and the rationale for the combination with the aspartyl protease inhibitor was to enhance the effects of the aspartyl protease inhibitor. No suggestion was made of combining the M1 Activator with the M2 Inhibitor, and both compounds would be capable of reaching and would be active in the central nervous system. U.S. Pat. No. 5,480,651 discloses use of agents that increase acetylcholine in the synapse or that activate the nicotinic acetylcholine receptors, followed by administration of an acetylcholine receptor antagonist to relieve craving associated with nicotine addiction. The preferred composition uses physostigmine which is an inhibitor of acetylcholinesterase, as opposed to a muscarinic Activator which would not activate the nicotinic acetylcholine receptors. WO 03/092580 discloses compounds that can act simultaneously as muscarinic Activators at certain receptor subtypes and antagonists at others. Groups have used various muscarinic Activators with muscarinic Inhibitors in the context of trying to differentiate the role of various muscarinic subtypes in drug pharmacology or normal physiology without suggesting a therapeutic use of the combination. Such studies include use of cellular assays starting from animal materials. (e.g., Iwanaga K. et al. *J Pharmacol. Sci.* 110:306. 2009). In US 2009/0318522, Paborji discloses use of a peripherally-acting muscarinic antagonist targeting the M2 and M3 receptors for the treatment of overactive bladder. The Paborji publication also discloses use of a peripherally-acting muscarinic M2/M3 agonist to counteract dry mouth associated with the peripherally-acting M2/M3 muscarinic antagonist. Paborji's approach does not, however, relate to activity at muscarinic receptors in the CNS, which is of critical importance for the work described herein, nor does it pertain to activity at either the M1 or M4 receptor. Paborji's approach is highly limited to a specific muscarinic inhibitor and does not provide any selection criteria to identify preferred or specific combinations of muscarinic Activators with the muscarinic antagonist, in spite of the prohibitively large number of potential combinations for which experimental testing could be done.

Method of Using Muscarinic Activators in Combination with Muscarinic Inhibitors

In one embodiment of the invention, one or more muscarinic Activators are used in combination with one or more Muscarinic Inhibitors for treatment of Muscarinic Disorders. In a preferred embodiment, such diseases or disorders include schizophrenia and Diseases Related to Schizophrenia. In another embodiment one or more muscarinic Activators are used in combination with one or more Muscarinic Inhibitors for treatment of Mood Disorders. In another embodiment, one or more muscarinic Activators are used with one or more muscarinic Inhibitors to treat Movement Disorders. In another embodiment, one or more muscarinic Activators are used with one or more muscarinic Inhibitors to treat Cognitive Disorders, including using the combination to enhance cognitive function not associated with a specific pathology. For instance, improvement in cognition could be important in undertaking complex tasks. In another embodiment, one or more muscarinic Activators are used with one or more muscarinic Inhibitors to treat Attention Disorders. Outside of disease treatment, enhancement of attention could improve learning and decrease symptoms associated with fatigue due to both lack of sleep and circadian rhythm disturbances such as jet lag. In another embodiment, one or more muscarinic Activators are used with one or more muscarinic Inhibitors to treat Addictive Disorders.

In another embodiment, the combination of one or more muscarinic Activators with one or more Muscarinic Inhibitors can be used to treat Muscarinic Disorders which are characterized by an amelioration of symptoms in response to inhibitors of cholinesterase enzymes. While cholinesterase inhibitors have proven therapeutic for certain diseases (e.g., Alzheimer's disease), the use of such inhibitors is limited due to toxicity. In fact, powerful chemical weapons such as sarin gas exert their toxic effects by inhibiting acetylcholinesterase (sarin gas material safety data sheet 103*d Congress, 2d Session.* United States Senate. May 25, 1994. http://www.gulfweb.org/bigdoc/report/appgb.html). The combination of one or more muscarinic Activators with one or more Muscarinic Inhibitors represents not only a safer method of treatment of those diseases shown to be response to cholinesterase inhibitors, but also a more effective one given the limitations on current cholinesterase inhibitors.

In one embodiment, the combination of one or more muscarinic Activators with one or more Muscarinic Inhibitors is used to treat an animal. In a further embodiment, the animal is a mammal. In a preferred embodiment, the mammal is a human being. In one embodiment, a single muscarinic Activator and a single muscarinic Inhibitor are used. In another embodiment more than one muscarinic Activator and/or more than one muscarinic Inhibitor is used.

In one embodiment, use of the Inhibitor decreases the side effects associated with use of the Activator. Such side effects include, but are not limited to, GI side effects, cardiac side effects, excessive sweating and excessive salivation. Use of one or more Inhibitors in combination with one or more Activators may allow the Activators to be used clinically when the Activators may not otherwise be used clinically due to the their side effects. In another embodiment, use of the Inhibitor in conjunction with the Activator allows for the Activator to achieve a higher maximum tolerated dose than the Activator would otherwise achieve.

Various time and resource intensive methods may be used to demonstrate both the efficacy of combination of the Activator and Inhibitor for the aforementioned embodiments. For example, animal models have been used to demonstrate the efficacy of new therapeutics for schizophrenia, including both pharmacological models (e.g., ketamine model) and genetic models. (e.g., DISC1 mouse) (Dawe G S et al. *AnnAcadMed Singapore.* 38:425. 2009; Desbonnet L. *Biochem Soc Trans.* 37:308. 2009; Geyer M A *Neurotox Res.* 14:71. 2008). Likewise, animal models including rodents, dogs and non-human primates can be used to demonstrate the side effect profile of pharmacological agents. Animal models serve as an experimental proxy for humans but may suffer from deficiencies associated with the physiological differences between human and animals and thus may have limited predictive power for translation to human experiments, particularly for central nervous system disorders. Alternatively, the combination can be tried in controlled clinical trials of people. Standard measures based on patient self-report can be used by those skilled in the art to assess various side effects such as GI discomfort. As another example, objective physiological measures (e.g., EKGs) may be used by those skilled in the art. A set of standard measures has also been developed to assess schizophrenia symptoms including the Brief Psychiatric Rating Scale (BPRS), the Positive and Negative Syndrome Scale (PANSS) and Clinical Global Impression (CGI). (Mortimer A M. *Br J Psychiatry Suppl.* 50:s7. 2007). Typically, clinical trials are conducted in a double blinded manner in which one group of patients receives an inactive placebo and the other group the active intervention.

In one embodiment of the invention, the muscarinic Activator is administered concurrently with the muscarinic Inhibitor. In another embodiment, the muscarinic Inhibitor is administered consecutively with the Activator. In further embodiment, the muscarinic Activator is administered prior to administration of the muscarinic Inhibitor. In another embodiment, the muscarinic Inhibitor is administered prior to administration of the muscarinic Activator. In one embodiment, the muscarinic Inhibitor is administered within one hour of administration of the muscarinic Activator. In another embodiment, the muscarinic Inhibitor is administered within 30 minutes of administration of the muscarinic Activator. In another embodiment, the muscarinic Inhibitor is administered within 10 minutes of administration of the muscarinic Activator. In another embodiment, the muscarinic Inhibitor is administered within one minute of administration of the muscarinic Activator. In another embodiment, the muscarinic Inhibitor is administered within 30 seconds of administration of the muscarinic Activator. Prior to the start of a drug regimen of the type outlined above, there may be a lead-in period that lasts from one to fourteen days. During this lead-in period, the muscarinic Inhibitor may be given by itself prior to the start of administration of the combination.

In one embodiment, from 10 micrograms to 10 grams of Activator is used in the combination with the Inhibitor. In another embodiment, from 1 milligram to 1 gram of Activator is used in the combination with the Inhibitor. In a preferred embodiment, from 5 to 500 milligrams of Activator is used. In one embodiment from 10 micrograms to 10 grams of Inhibitor is used in the combination with the Activator. In another embodiment, from 1 milligram to 1 gram of Inhibitor is used in the combination with the Activator. In a preferred embodiment, from 2.5 milligrams and 200 milligrams of Inhibitor is used.

In one embodiment, the muscarinic Activator and Muscarinic Inhibitor are administered to a patient 6 times during a 24-hour period. In another embodiment, the muscarinic Activator and Muscarinic Inhibitor are administered to a patient 5 times during a 24-hour period. In another embodiment, the muscarinic Activator and Muscarinic Inhibitor are administered to a patient 4 times during a 24-hour period. In a preferred embodiment, the muscarinic Activator and Muscarinic Inhibitor are administered to a patient 3 times during a 24-hour period. In another preferred embodiment, the muscarinic Activator and Muscarinic Inhibitor are administered to a patient 2 times during a 24-hour period. In another preferred embodiment, the muscarinic Activator and Muscarinic Inhibitor are administered to a patient one time during a 24-hour period.

In Silico Testing of Muscarinic Combinations

There are 65 unique muscarinic Activators and 114 unique muscarinic Inhibitors that are currently known (Adis R&D Insight™, PubMed, Web of Science, U.S. FDA Orange Book, U.S. Pat. No. 5,852,029). Therefore, there exist 7,410 potential combinations in which a single muscarinic Activator could be paired with a single muscarinic Inhibitor. If one were to combine more than one muscarinic Activator with one or more muscarinic Inhibitors, then the number of combinations would be even greater. While a number of animal models exist for relevant diseases such as schizophrenia (Dawe G S et al. *Ann Acad Med Singapore.* 38:425. 2009; Desbonnet L. *Biochem Soc Trans.* 37:308. 2009; Geyer M A *Neurotox Res.* 14:71. 2008), animal models of complex diseases such as schizophrenia are imperfect, and thus the ability to predict human efficacy and side effect burden based on animal data may be limited. Likewise, it is possible to test combinations in humans suffering from a particular disease such as schizophrenia where there exist standard measuring scales (Mortimer A M. *Br J Psychiatry Suppl.* 50:s7. 2007) for both efficacy of disease treatment as well as side effects. However, testing such a large number of combinations in either animal models of disease or more importantly in human clinical trials is practically impossible as it would be prohibitively expensive, and could take decades due to limitations in the number of existing skilled investigators and required time for patient recruitment.

Without a method of testing and predicting the efficacy of a given combination, it is extremely difficult to predict a priori if such a combination will be efficacious. For instance, Medina et al. gave the muscarinic agonist xanomeline and the muscarinic antagonist methscopolamine to investigate whether syncope, which is a side effect observed with xanomeline, can be mediated by muscarinic antagonists (Medina et al. *Hypertension.* 29: 828. 1997). The group observed no effect on syncope, which may reflect the lack of involvement of the muscarinic system in syncope or, alternatively, may reflect the incorrect selection of a muscarinic combination. Likewise, Mouradian et al. documented use of the muscarinic agonist RS-86 with the anticholinergic agent glycopyrrolate for treatment of Alzheimer's Disease (Mouradian et al. *Neurology.* 38:606. 1988). The approach did not result in any improvement in cognition despite use of escalating amounts of RS-86. US 2006/0194831 discloses use of a derivative of clozapine to activate muscarinic receptors. While US 2006/0194831 discloses that the use of the clozapine derivative can be combined with another therapy selected from a broad list of therapies including use of a muscarinic antagonist, the publication provides no guidance or reasoning, for example, as to why a particular agent should be selected from the broad list for combination with the clozapine derivative, or why such a combination would be useful. U.S. Pat. No. 5,852,029, which discloses a particular muscarinic agonist, mentions potential use of the particular agonist with muscarinic antagonists to help eliminate side effects but does not provide any criteria for selecting an appropriate antagonist.

Lack of success by groups such as Mouradian et al. points to the need to carefully select and ideally test combinations of muscarinic Activators and Inhibitors. Given the impractical nature of physically testing such a large number of combinations, we created an algorithm for in silico testing to perform the extremely difficult task of predicting a priori, without in vivo testing, if a given combination will be efficacious and safe. In order to carry out the in-silico testing based on the algorithm, we created an extensive database which captured the known information about muscarinic Activators and Inhibitors. The process by which we created this unique algorithm, as well as the database of muscarinic agents and their properties, was both multi-phased and resource-intensive. First, we created a list of all known muscarinic Activators and Inhibitors. Next, we selected properties of muscarinic agents that are useful in predicting an efficacious and safe combination and determined the relative importance of each property. We then embarked on an exhaustive data-collection process to, wherever possible, gather data related to each property for each muscarinic Activator and Inhibitor. With this data on-hand, we then created a computer-based algorithm, whereby a score is calculated for each property and each combination, such that these scores are then used to generate an overall score for each combination. The scoring system was created such that higher total scores ("Theta Scores") are applied to combinations with a higher probability to be efficacious with acceptable side effects. Therefore, by testing each combination with the algorithm, we created a prioritized list of combinations whereby combinations with higher scores are more attractive candidates for clinical testing. Given the impracticality of testing every possible combination in vivo, prioritization to select combinations for testing in humans is critical.

In order to evaluate different combinations of muscarinic Activator and Inhibitors, we created a proprietary database of all known muscarinic Activators and Inhibitors (see Tables 1 and 2). This database was created through systematic reviews of a variety of resources in search of all current and past programs related to muscarinic Activators and Inhibitors. Our reviews included scholarly literature databases, such as PubMed and Web of Science, patent databases, such as Delphion, and pharmaceutical research and development databases, such as Adis R&D Insight™. We also reviewed drug package inserts, news databases, company websites, and conference abstracts. In all, we reviewed several thousand journal publications, patents, Adis records, and other documents to generate a comprehensive database of 65 muscarinic Activators and 114 muscarinic Inhibitors.

We then selected properties useful in predicting whether a given combination will be efficacious with acceptable side effects. We determined, in other words, the criteria by which each combination may be evaluated in order to generate a quantitative, predictive assessment. This process of selecting relevant properties was driven by rigorous internal analyses and resulted in the identification of several properties that are typically not considered, and/or that are typically thought to be unfavorable, but which we treated as favorable. The combination therapy approach in this application is significantly different from typical combination therapy approaches, which entail looking for synergistic efficacy of two agents. In the present invention, we look for one agent to eliminate the effects of the other agent, which leads to unorthodox criteria for drug selection. For example, we evaluated each muscarinic Inhibitor based on efficacy data such that, in some cases, low or poor efficacy data was rewarded. Also, contrary to typical approaches, in some cases we rewarded muscarinic Inhibitors for the side effects they exhibited during clinical development. Since most muscarinic Inhibitors were tested for unrelated indications, such as overactive bladder, efficacy for these unrelated indications may be undesirable and may be predictive of a combination with potentially unacceptable side effects. For instance, excessive urination is not a commonly reported side effect of muscarinic Activators. Therefore, having Inhibitors that have the greatest ability to decrease micturition may present the greatest risk of causing urinary retention without providing a benefit in the combination.

We rewarded certain side effects, particularly those known to be associated with peripheral anticholinergic effects, because they may counteract or lessen the impact of muscarinic Activator side effects. This combination of rewarding side effects and rewarding poor efficacy leads to the selection of a muscarinic Inhibitor that will have physiological effects throughout the periphery, which is desired for the elimination of muscarinic Activator side effects. For example, if a compound demonstrated efficacy for the treatment of overactive bladder without any side effects, this would suggest that the compound was inhibiting muscarinic receptors in the bladder, but not in the gastrointestinal tract or in the salivary glands to a significant degree. Although such as compound would be ideal for a drug whose intended purpose is the treatment of overactive bladder, such a compound would be unfavorable for the uses described herein. A more favorable Inhibitor for the envisioned combination would demonstrate pharmacological effects (i.e., side effects observed when treating overactive bladder) in the same organs where the Activator causes undesired side effects (e.g., the gastrointestinal tract). The rewarding of side effects and penalizing of efficacy stands in contrast to the typical method for selecting pharmaceutical agents.

Our intensive selection process resulted in 95 relevant properties, on the basis of which each of the 7,410 combinations of known muscarinic Activators and Inhibitors would be evaluated. The properties fell into three general categories: properties related exclusively to muscarinic Activators; properties related exclusively to muscarinic Inhibitors; and properties that combined attributes of both the Activator and Inhibitor. These classifications are discussed below in detail.

To collect data for each muscarinic Activator and Inhibitor based on each property, we embarked on a rigorous data collection process using many of the same resources as those used in generating a database of all known muscarinic Activators and Inhibitors. Again, our review spanned scholarly literature databases, such as PubMed and Web of Science, patent databases, such as Delphion, pharmaceutical research and development databases, such as Adis R&D Insight™ and the U.S. FDA Orange Book, as well as package inserts and other resources. This process differed, however, in the detailed and often quantitative nature of the information extracted. For example, we gathered and categorized all known efficacy and side effect data for each muscarinic Activator and Inhibitor. We also gathered all known data related to pharmacokinetics and pharmacodynamics. As new data becomes available for compounds currently in our database, or as information regarding potential new entries for our database becomes available, database updates may be made, which would yield new theta scores. For example, MCD 386 is a muscarinic Activator for which additional data could result in increased theta scores for muscarinic Activator and Inhibitor combinations that include MCD 386.

Using these data, we then created a computer-based algorithm to quantify the relative probability that each muscarinic Activator and Inhibitor combination will be efficacious with acceptable side effects. The scoring system functions by applying a score to each combination based on each property, which we call a p-score. Each p-score contributed to an overall calculation, such that a high p-score signified that a combination has an increased likelihood of being efficacious with acceptable side effects based on a given property. Since the algorithm tested a total of 7,410 possible combinations, each of which was evaluated based on 95 p-scores, the algorithm summed a total of 703,950 p-scores in calculating a unique overall score (a "Theta Score") for each combination (see FIG. 1).

Given the varied nature of data from one property to the next, a variety of scoring methodologies were used to generate p-scores. In all cases, scoring methodologies were consistent within a given property and generated a maximum value of 10, which was then multiplied by a "weight factor." Weight factors were used to reflect the importance of each property in predicting the probability that a combination is efficacious with acceptable side effects. Some properties, such as those relating to the demonstration of efficacy for an agonist, have a stronger impact in assessing a preferred combination and were thus weighted more heavily. The baseline weight factor for all properties was 1, and the maximum weight factor used was 2.

The primary methodologies used in generating p-scores were ranking-based scoring, binary scoring, and scoring by value cut-off. The mechanics of each of these methodologies are detailed below:

Ranking-based p-scores were generated using quantitative data, such as efficacy measurements, and awarding the highest value (e.g., a score of 10) to the most preferable data point, and the lowest value (e.g., a score of 0) to the least preferable data point. The remaining values were then distributed linearly, such that less preferable data points were awarded proportionally lower scores. Finally, a weight factor was applied to each value by multiplying each score by a pre-determined weight that reflected the importance of the given property. Take, for example, the case where three muscarinic Inhibitors (Inhibitor A, Inhibitor B, and Inhibitor C) are evaluated based on the demonstrated reduction in urinary frequency (number of micturitions per 24 hours), such that the minimum reduction, or lowest efficacy, is desired. In this case, Inhibitor A shows a reduction of 1 micturition per 24 hours, while Inhibitors B and C show values of 2 and 4 respectively. To calculate each p-score, since Inhibitor A demonstrated the most desirable results, we first must give Inhibitor A a proportionally higher value than B or C (e.g., Inhibitors A, B, and C are given values of 1, ½, and ¼, respectively). We then linearly distribute these values such that Inhibitor A receives a score of 10, Inhibitor B a score of 5, and Inhibitor C a score of 2.5. Finally, these scores are multiplied by a weight factor, which in this case would be 1, giving final p-scores of 10, 5, and 2.5.

Binary p-scores were generated by assigning one of two values relating to a binary property. Take, for example, the case of two muscarinic Activators, A and B, which are evaluated based on whether they have shown efficacy in human trials. Muscarinic Activator A, which has shown efficacy, is awarded a value of 10, while B, which has not, receives a score of 0. Since this important property has a weight factor of 2, muscarinic Activators A and B receive final p-scores of 20 and 0, respectively.

Value cut-off p-scores were applied based on the group into which a given value fell. This methodology was used for non-binary cases where a ranking methodology is not preferred or possible (e.g., scoring qualitative data, or scoring quantitative data in which cut-offs are relevant). In these cases, muscarinic Activators or Inhibitors whose values fall into the most desirable category are awarded values of 10 (prior to multiplication by the corresponding weight factor).

The p-scores applied to each combination were summed to generate three unique Subscores: the Activator Independent Subscore, the Inhibitor Independent Subscore, and the Combination Subscore. The Activator Independent Subscore represents an evaluation of each agonist based on properties that are independent of the antagonist with which it is combined (e.g., the demonstration of efficacy in human trials). Similarly, the Inhibitor Independent Subscore represents an evaluation of each antagonist based on properties that are independent of the agonist with which it is combined (e.g., level of CNS penetrance). The Combination Subscore, in contrast, represents an evaluation based on properties in which characteristics of both the agonist and antagonist are relevant (e.g., similarity of $T_{max}$ based on pharmacokinetic studies). For both the Activator Independent Subscore and the Inhibitor Independent Subscore, the value was calculated by summing each p-score and then normalizing each score such that the highest-ranking entry was given a score of 100. Each lower ranking entry was thus increased or decreased proportionally by the same factor as the highest-ranking entry. In calculating the Combination Subscore, the same principle was applied; however, the maximum score given was 50.

Ultimately, the algorithm generated a final "Theta Score" for each combination such that, as the theta score increased, so did the probability that the combination would produce efficacy with acceptable side effects. The Theta Score was calculated by summing the three Subscores.

TABLE 1

List of Muscarinic Activators

| | |
|---|---|
| 1 | A 72055 |
| 2 | AF 125 |
| 3 | AF 150(S) |
| 4 | AF 185 |
| 5 | Alvameline |
| 6 | Amifostine |
| 7 | Arecoline transdermal-Cogent Pharmaceuticals |
| 8 | Cevimeline |
| 9 | CI 1017 |
| 10 | CMI 1145 |
| 11 | CMI 936 |
| 12 | CS 932 |
| 13 | DM 71 |
| 14 | FPL 14995 |
| 15 | GSK 1034702 |
| 16 | Himbacine |
| 17 | Itameline |
| 18 | KST 2818 |
| 19 | KST 5410 |

TABLE 1-continued

List of Muscarinic Activators

| | |
|---|---|
| 20 | KST 5452 |
| 21 | L 670548 |
| 22 | L 689660 |
| 23 | L 696986 |
| 24 | L 705106 |
| 25 | LY 316108 |
| 26 | MCD 386 |
| 27 | Milameline |
| 28 | Muscarinic receptor agonists-ACADIA/Allergan |
| 29 | NC 111585 |
| 30 | Nebracetam |
| 31 | NGX 267 |
| 32 | Nordozapine |
| 33 | ORG 20091 |
| 34 | PD 141606 |
| 35 | PD 142505 |
| 36 | PD 151832 |
| 37 | PDC 008004 |
| 38 | Pilocarpine |
| 39 | Pilocarpine-Controlled Therapeutics |
| 40 | PTAC |
| 41 | Anavex Life Sciences preclinical muscarinic activator |
| 42 | Eli Lilly preclinical M1 receptor muscarinic activator |
| 43 | Eli Lilly preclinical M4 receptor muscarinic activator |
| 44 | TorryPines Therapeutics preclinical muscarinic activator |
| 45 | Banyu preclinical muscarinic activator |
| 46 | Mithridion preclinical muscarinic activator |
| 47 | ACADIA/Sepracor preclinical muscarinic activator |
| 48 | ACADIA preclinical muscarinic activator |
| 49 | RU 35963 |
| 50 | Sabcomeline |
| 51 | SDZ 210086 |
| 52 | SR 46559A |
| 53 | SR 96777A |
| 54 | Stacofylline |
| 55 | Talsadidine |
| 56 | Tazomeline |
| 57 | Thiopilocarpine |
| 58 | Ticalopride |
| 59 | U 80816 |
| 60 | Vedaclidine |
| 61 | WAY 131256 |
| 62 | WAY 132983 |
| 63 | Xanomeline |
| 64 | YM 796 |
| 65 | YM 954 |

TABLE 2

List of Muscarinic Inhibitors

| | |
|---|---|
| 1 | Aclidinium bromide |
| 2 | Aclidinium bromide/formoterol |
| 3 | Acotiamide |
| 4 | AH 9700 |
| 5 | Alvameline |
| 6 | AQRA 721 |
| 7 | AQRA 741 |
| 8 | AZD 9164 |
| 9 | BIBN 99 |
| 10 | CEB 1957 |
| 11 | Clozapine extended release-Azur Pharma |
| 12 | Darenzepine |
| 13 | Darifenacin |
| 14 | Darotropium bromide |

TABLE 2-continued

List of Muscarinic Inhibitors

| | |
|---|---|
| 15 | Dextromequitamium iodide |
| 16 | Ebeinone |
| 17 | Esoxybutynin |
| 18 | Espatropate |
| 19 | Fesoterodine |
| 20 | Glycopyrrolate/indacaterol |
| 21 | Glycopyrronium bromide |
| 22 | GSK 1160724 |
| 23 | GSK 202405 |
| 24 | GSK 573719 |
| 25 | GSK 656398 |
| 26 | GSK 961081 |
| 27 | GYKI 46903 |
| 28 | Homatropine methylbromide |
| 29 | Imidafenacin |
| 30 | Inhaled glycopyrrolate-Novartis |
| 31 | Ipratropium bromide dry-powder inhalation-Dura/Spiros |
| 32 | Ipratropium bromide dry-powder inhalation-M1 Laboratories |
| 33 | Ipratropium bromide hydrofluoroalkane inhalator-Boehringer Ingelheim |
| 34 | Ipratropium bromide intranasal-Chiesi |
| 35 | Ipratropium bromide metered solution inhalation Sheffield |
| 36 | Ipratropium bromide/xylometazoline |
| 37 | J 104129 |
| 38 | J 106366 |
| 39 | L 696986 |
| 40 | LAS 35201 |
| 41 | Levosalbutamol/ipratropium inhalation solution-Arrow International Limited/S |
| 42 | Liriodenine |
| 43 | LK 12 |
| 44 | Mequitamium iodide |
| 45 | Methantheline |
| 46 | Methantheline bromide |
| 47 | Methscopolamine bromide |
| 48 | N-butylscopolamine |
| 49 | N-methylatropine |
| 50 | NPC 14695 |
| 51 | NX 303 |
| 52 | Otenzepad |
| 53 | Oxybutynin-Labopharm |
| 54 | Oxybutynin-Penwest Pharmaceuticals |
| 55 | Oxybutynin chloride-ALZA |
| 56 | Oxybutynin intravesical-Situs |
| 57 | Oxybutynin transdermal-Schwarz Pharma |
| 58 | Oxybutynin transdermal-Watson |
| 59 | Oxybutynin transdermal gel-Antares |
| 60 | Oxybutynin transmucosal-Auxilium |
| 61 | Oxybutynin vaginal-Barr Laboratories |
| 62 | PG 1000 |
| 63 | Pirenzepine ophthalmic |
| 64 | Pirmenol |
| 65 | PNU 200577 |
| 66 | Promethazine/hydrocodone/paracetamol-Charleston Laboratories |
| 67 | Propantheline |
| 68 | Propantheline bromide |
| 69 | Propiverine |
| 70 | PSD 506 |
| 71 | PTAC |
| 72 | QAT 370 |
| 73 | Almirall muscarinic Inhibitor |
| 74 | Anavex Life Sciences primary muscarinic Inhibitor |
| 75 | Anavex Life Sciences secondary muscarinic inhibitor |

TABLE 2-continued

List of Muscarinic Inhibitors

| | |
|---|---|
| 76 | FF2-Nuada |
| 77 | GlaxoSmithKline/Theravance |
| 78 | Chiesi Farmaceutici/SALVAT muscarinic inhibitor |
| 79 | UCB muscarinic Inhibitor |
| 80 | Theravance primary muscarinic Inhibitor |
| 81 | Theravance secondary muscarinic Inhibitor |
| 82 | Novartis muscarinic Inhibitor |
| 83 | ACADIA/Sepracor muscarinic Inhibitor |
| 84 | Safetek muscarinic Inhibitor |
| 85 | Revatropate |
| 86 | Rispenzepine |
| 87 | RL 315535 |
| 88 | RO 465934 |
| 89 | SCH 211803 |
| 90 | SCH 57790 |
| 91 | Scopolamine intranasal-Nastech |
| 92 | Scopolamine transmucosal-Anesta |
| 93 | Secoverine |
| 94 | S-ET 126 |
| 95 | Sintropium bromide |
| 96 | Solifenacin |
| 97 | Solifenacin/tamsulosin |
| 98 | SVT 40776 |
| 99 | TD 6301 |
| 100 | Telenzepine |
| 101 | Temiverine |
| 102 | Tiotropium bromide |
| 103 | Tolterodine |
| 104 | Tolterodine/tamsulosin |
| 105 | Tropenzilium |
| 106 | Trospium chloride |
| 107 | Trospium chloride controlled release |
| 108 | Trospium chloride inhalation |
| 109 | V 0162 |
| 110 | YM 35636 |
| 111 | YM 46303 |
| 112 | YM 53705 |
| 113 | YM 58790 |
| 114 | Zamifenacin |

The algorithm was structured with inputs according to the following 3 tables. The Property, Scoring Methodology, Criteria for a High Score, and Weight columns in each table represent the underlying inputs and mechanics used in calculating each Subscore.

TABLE 3

Mechanics of Activator Independent Subscore
Activator Subscore Mechanics

| Count | Property Category | Property | Scoring Methodology | Criteria for a High Score | Weight Factor |
|---|---|---|---|---|---|
| 1 | Development | Highest Phase | Unique value assigned to each dev. stage | High stage of development | 1 |
| 2 | Development | Highest Phase CNS | Unique value assigned to each dev. stage | High stage of development | 1 |
| 3 | Development | Highest Phase US | Unique value assigned to each dev. stage | High stage of development | 1 |
| 4 | ROA | Route of Administration | Unique value assigned to each ROA | Oral | 1 |
| 5 | Pharmacokinetics | Tmax | Ranked by Tmax value | High Tmax | 1 |
| 6 | Pharmacokinetics | T(½) | Ranked by T(½) value | High T(½) | 1 |
| 7 | Efficacy | Demonstrated Efficacy | Binary scoring | Efficacy shown | 2 |
| 8 | Efficacy | Demonstrated Efficacy in Cognition | Binary scoring | Efficacy shown | 2 |
| 9 | Efficacy | Demonstrated Efficacy in | Binary scoring | Efficacy shown | 2 |
| 10 | Receptor Selectivity | M2 Agonist? | Binary scoring | Not M2 Agonist | 1 |
| 11 | Receptor Selectivity | M3 Agonist? | Binary scoring | Not M3 agonist | 1 |
| 12 | Receptor Selectivity | M1/M2 ratio | Ranked by ratio value | High ratio | 1 |
| 13 | Receptor Selectivity | M1/M3 ratio | Ranked by ratio value | High ratio | 1 |
| 14 | Receptor Selectivity | M1/M5 ratio | Ranked by ratio value | High ratio | 1 |
| 15 | Receptor Selectivity | M4/M2 ratio | Ranked by ratio value | High ratio | 1 |
| 16 | Receptor Selectivity | M4/M3 ratio | Ranked by ratio value | High ratio | 1 |
| 17 | Receptor Selectivity | M4/M5 ratio | Ranked by ratio value | High ratio | 1 |
| 18 | Receptor Selectivity | M2/M3 ratio | Ranked by ratio value | Close to 1 | 1 |

TABLE 3-continued

Mechanics of Activator Independent Subscore
Activator Subscore Mechanics

| Count | Property Category | Property | Scoring Methodology | Criteria for a High Score | Weight Factor |
|---|---|---|---|---|---|
| 19 | Receptor Selectivity | M5/M2 ratio | Ranked by ratio value | Close to 1 | 1 |
| 20 | Receptor Selectivity | M5/M3 ratio | Ranked by ratio value | Close to 1 | 1 |

TABLE 4

Mechanics of Inhibitor Independent Subscore Inhibitor Subscore Mechanics

| Count | Property Category | Property | Scoring Methodology | Criteria for High Score | Weight Factor |
|---|---|---|---|---|---|
| 1 | Development | Highest Phase | Unique value assigned to each dev. stage | High stage of development | 1 |
| 2 | Development | Highest Phase US | Unique value assigned to each dev. stage | High stage of development | 1 |
| 3 | ROA | Route of Administration | Unique value assigned to each ROA\ | Oral | 1 |
| 4 | Pharmacokinetics | Tmax | Ranked by Tmax value | High Tmax | 1 |
| 5 | Pharmacokinetics | T(½) | Ranked by T(½) value | High T(½) | 1 |
| 6 | CNS Penetrance | CNS Penetrance | Unique value assigned based on H, M, L penetrance | Low penetrance | 2 |
| 7 | Receptor Selectivity | M2/M1 ratio | Ranked by ratio value | High ratio | 1 |
| 8 | Receptor Selectivity | M2/M4 ratio | Ranked by ratio value | High ratio | 1 |
| 9 | Receptor Selectivity | M3/M1 ratio | Ranked by ratio value | High ratio | 1 |
| 10 | Receptor Selectivity | M3/M4 ratio | Ranked by ratio value | High ratio | 1 |
| 11 | Efficacy | Urinary Frequency (# Micturitions per 24 hrs)-- Reduction | Ranked by efficacy value | Low efficacy | 1 |
| 12 | Efficacy | Urinary Frequency (# Micturitions/24 hrs)-- % Reduction | Ranked by efficacy value | Low efficacy | 1 |
| 13 | Efficacy | Urinary Frequency (# Micturitions/24 hrs)-- % Reduction over Placebo | Ranked by efficacy value | Low efficacy | 1 |
| 14 | Efficacy | Urinary Frequency (# Micturitions/24 hrs)-- Reduction over Placebo | Ranked by efficacy value | Low efficacy | 1 |
| 15 | Efficacy | Volume Voided/micturition (mL)--Reduction | Ranked by efficacy value | Low efficacy | 1 |
| 16 | Efficacy | Volume Voided/micturition (mL)--% Reduction | Ranked by efficacy value | Low efficacy | 1 |
| 17 | Efficacy | Volume Voided/micturition (mL)--% Reduction over Placebo | Ranked by efficacy value | Low efficacy | 1 |
| 18 | Efficacy | Volume Voided/micturition (mL)--% Reduction over Placebo | Ranked by efficacy value | Low efficacy | 1 |
| 19 | Efficacy | # of Incontinence Eps/24 hours--% Reduction | Ranked by efficacy value | Low efficacy | 1 |
| 20 | Efficacy | # of Incontinence Eps/24 hours--% Reduction | Ranked by efficacy value | Low efficacy | 1 |

TABLE 4-continued

Mechanics of Inhibitor Independent Subscore Inhibitor Subscore Mechanics

| Count | Property Category | Property | Scoring Methodology | Criteria for High Score | Weight Factor |
|---|---|---|---|---|---|
| 21 | Efficacy | # of Incontinence Eps/week--% Reduction | Ranked by efficacy value | Low efficacy | 1 |
| 22 | Efficacy | # of incontinence Eps/week--% Reduction | Ranked by efficacy value | Low efficacy | 1 |
| 23 | Efficacy | # Urge incontinence eps/24 hrs--% Reduction | Ranked by efficacy value | Low efficacy | 1 |
| 24 | Efficacy | # Urge incontinence eps/24 hrs--% Reduction | Ranked by efficacy value | Low efficacy | 1 |
| 25 | Efficacy | # Urge incontinence eps/week--% Reduction | Ranked by efficacy value | Low efficacy | 1 |
| 26 | Efficacy | # Urge incontinence eps/week--% Reduction | Ranked by efficacy value | Low efficacy | 1 |
| 27 | Adverse Events | Dry Mouth--% increase over placebo | Ranked by AE value | Low AE values | 1 |
| 28 | Adverse Events | Constipation--% increase over placebo | Ranked by AE value | Low AE values | 1 |
| 29 | Adverse Events | Dyspepsia--% increase over placebo | Ranked by AE value | Low AE values | 1 |
| 30 | Adverse Events | Abdominal Pain--% increase over placebo | Ranked by AE value | Low AE values | 1 |
| 31 | Adverse Events | Dry Mouth--absolute % values | Ranked by AE value | Low AE values | 1 |
| 32 | Adverse Events | Constipation--absolute % values | Ranked by AE value | Low AE values | 1 |
| 33 | Adverse Events | Dyspepsia--absolute % values | Ranked by AE value | Low AE values | 1 |
| 34 | Adverse Events | Abdominal Pain--absolute % values | Ranked by AE value | Low AE values | 1 |
| 35 | Adverse Events | Constipation aggravated | Ranked by AE value | Low AE values | 1 |
| 36 | Adverse Events | Nausea | Ranked by AE value | Low AE values | 1 |
| 37 | Adverse Events | Abdominal Distension | Ranked by AE value | Low AE values | 1 |
| 38 | Adverse Events | Flatulence | Ranked by AE value | Low AE values | 1 |
| 39 | Adverse Events | Diarrhea | Ranked by AE value | Low AE values | 1 |
| 40 | Adverse Events | Vomiting | Ranked by AE value | Low AE values | 1 |
| 41 | Adverse Events | UTI | Ranked by AE value | Low AE values | |
| 42 | Adverse Events | Upper Respiratory tract infection | Ranked by AE value | Low AE values | 1 |
| 43 | Adverse Events | Influenza | Ranked by AE value | Low AE values | 1 |
| 44 | Adverse Events | Pharyngitis | Ranked by AE value | Low AE values | 1 |
| 45 | Adverse Events | Headache | Ranked by AE value | Low AE values | 1 |
| 46 | Adverse Events | Dizziness | Ranked by AE value | Low AE values | 1 |
| 47 | Adverse Events | Vision Blurred | Ranked by AE value | Low AE values | 1 |
| 48 | Adverse Events | Dry Eyes | Ranked by AE value | Low AE values | 1 |
| 49 | Adverse Events | Urinary Retention | Ranked by AE value | Low AE values | 1 |
| 50 | Adverse Events | Dysuria | Ranked by AE value | Low AE values | 1 |
| 51 | Adverse Events | Edema Lower Limb | Ranked by AE value | Low AE values | 1 |
| 52 | Adverse Events | Edema peripheral | Ranked by AE value | Low AE values | 1 |
| 53 | Adverse Events | Fatigue | Ranked by AE value | Low AE values | 1 |
| 54 | Adverse Events | Depression | Ranked by AE value | Low AE values | 1 |

TABLE 4-continued

Mechanics of Inhibitor Independent Subscore Inhibitor Subscore Mechanics

| Count | Property Category | Property | Scoring Methodology | Criteria for High Score | Weight Factor |
|---|---|---|---|---|---|
| 55 | Adverse Events | Insomnia | Ranked by AE value | Low AE values | 1 |
| 56 | Adverse Events | Cough | Ranked by AE value | Low AE values | 1 |
| 57 | Adverse Events | Dry Throat | Ranked by AE value | Low AE values | 1 |
| 58 | Adverse Events | Hypertension | Ranked by AE value | Low AE values | 1 |
| 59 | Adverse Events | Asthenia | Ranked by AE value | Low AE values | 1 |
| 60 | Adverse Events | Nasal dryness | Ranked by AE value | Low AE values | 1 |
| 61 | Adverse Events | Back pain | Ranked by AE value | Low AE values | 1 |
| 62 | Adverse Events | ALT increased | Ranked by AE value | Low AE values | 1 |
| 63 | Adverse Events | GGT increased | Ranked by AE value | Low AE values | 1 |
| 64 | Adverse Events | Rash | Ranked by AE value | Low AE values | 1 |

Note:
ALT = Alanine transaminase;
GGT = Gamma-glutamyltransferase

TABLE 5

Mechanics of Combination Subscore - Combination Subscore Mechanics

| Count | Property Category | Property | Scoring Methodology | Criteria for a High Score | Weight Factor |
|---|---|---|---|---|---|
| 1 | Pharmacokinetics | Tmax | Unique value given based on closeness of Tmax | Close Tmax values | 1 |
| 2 | Pharmacokinetics | T(½) | Unique value given based on closeness of T(½) | Close T(½) values | 1 |
| 3 | Metabolism | Drug-drug interaction potential | Unique value assigned based on H, M, or L degree of interaction, specifically regarding CYP 450 | Low overall risk of drug-drug interaction | 1 |
| 4 | Receptor Selectivity | (M1 Activator selectivity/M1 Inhibitor selectivity) ratio | Ranked by ratio value | High ratio value (devalue if Inhibitor acts on M1, Activator is weak M1 Activator) | 1 |
| 5 | Receptor Selectivity | (M4 Activator selectivity/M4 Inhibitor selectivity) ratio | Ranked by ratio value | High ratio value (devalue if Inhibitor acts on M4, Activator is weak M4 Activator) | 1 |
| 6 | Receptor Selectivity | (M3 Activator selectivity/M3 Inhibitor selectivity) ratio | Ranked by ratio value | Low ratio value (With M3 Activator, M3 Inhibitor is desired) | 1 |
| 7 | Receptor Selectivity | (M2 Activator selectivity/M2 Inhibitor selectivity) ratio | Ranked by ratio value | Low ratio value (If M2 Activator, M2 Inhibitor is desired) | 1 |
| 8 | Receptor Selectivity | (M5 Activator selectivity/M5 Inhibitor selectivity) ratio | Ranked by ratio value | High ratio value | 1 |
| 9 | Receptor Selectivity | M2/M3 ratio comparison | Ranked by ratio value | Ratio value close to 1 | 1 |

TABLE 5-continued

Mechanics of Combination Subscore - Combination Subscore Mechanics

| Count | Property Category | Property | Scoring Methodology | Criteria for a High Score | Weight Factor |
|---|---|---|---|---|---|
| 10 | Efficacy | Reward specific cases of Inhibitor AEs if "offsetting" an Activator AE | Case specific | Case specific | 1 |
| 11 | Adverse Events | Reward specific cases of Inhibitor AEs if "offsetting" an Activator AE | Case specific | Case specific | 1 |

Note:
In cases where Activators inhibits a receptor, or where an Inhibitor activates a receptor, receptor selectivity ratios are changed to equal one divided by the ratio for determining the p-score.

TABLE 6

Top 15 Combinations by Theta Score

| Combination ID | Combination | Theta Score | Activator Independent Subscore | Inhibitor Independent Subscore | Combination Subscore |
|---|---|---|---|---|---|
| 6355 | Xanomeline & Trospium chloride | 250 | 100 | 100 | 50 |
| 5003 | Sabcomeline & Trospium chloride | 245 | 95 | 100 | 50 |
| 2611 | Milamaine & Trospium chloride | 243 | 98 | 100 | 45 |
| 6346 | Xanomeline & Tolterodine | 241 | 100 | 91 | 50 |
| 2602 | Milameline & Tolterodine | 239 | 98 | 91 | 50 |
| 5005 | Sabcomeline & Trospium chloride controlled release | 238 | 95 | 93 | 50 |
| 6357 | Xanomeline & Trospium chloride controlled release | 238 | 100 | 93 | 45 |
| 2613 | Milameline & Trospium chloride controlled release | 236 | 98 | 93 | 45 |
| 6347 | Xanomeline & Darifenacin | 235 | 100 | 95 | 40 |
| 6348 | Xanomeline & Solifenacin | 234 | 100 | 94 | 40 |
| 4996 | Sabcomeline & Solifenacin | 229 | 95 | 94 | 40 |
| 5523 | Talsaclidine & Trospium chloride | 224 | 94 | 100 | 30 |
| 635 | Cevimeline & Trospium chloride | 219 | 89 | 100 | 30 |
| 5515 | Talsaclidine & Darifenacin | 219 | 94 | 95 | 30 |
| 5516 | Talsaclidine & Solifenacin | 218 | 94 | 94 | 30 |
| 5525 | Talsaclidine & Trospium chloride controlled release | 217 | 94 | 93 | 30 |
| 5514 | Talsaclidine & Tolterodine | 215 | 94 | 91 | 30 |
| 6349 | Xanomeline & Fesoterodine | 215 | 100 | 85 | 30 |
| 627 | Cevimeline & Darifenacin | 214 | 89 | 95 | 30 |
| 637 | Cevimeline & Trospium chloride controlled release | 212 | 89 | 93 | 30 |

In a preferred embodiment of the invention, a combination of a muscarinic Activator and a muscarinic Inhibitor with a theta score of 230 or greater as determined by in silico testing using the above described algorithm is used. In another embodiment of the invention, a combination of a muscarinic Activator and a muscarinic Inhibitor with a theta score of 200 or greater as determined by in silico testing using the above described algorithm is used. In another embodiment of the invention, a combination of a muscarinic Activator and a muscarinic Inhibitor with a theta score of 150 or greater as determined by in silico testing using the above described algorithm is used. In a further embodiment of the invention, a combination of a muscarinic Activator and a muscarinic Inhibitor with a theta score of 149 or lower as determined by in silico testing using the above described algorithm is used.

In one embodiment, xanomeline is used as the muscarinic Activator in combination with the muscarinic Inhibitor. In another embodiment, xanomeline is administered to a patient from one time to five times during a 24-hour period. In a preferred embodiment, xanomeline is administered from one time to three times during a 24-hour period. In another embodiment, from 25 milligrams to 700 milligrams of xanomeline is used during a vperiod. In a preferred embodiment, from 75 milligrams to 300 milligrams of xanomeline is used during a 24-hour period.

In one embodiment, sabcomeline is used as the muscarinic Activator in combination with the muscarinic Inhibitor. In another embodiment, sabcomeline is administered to a patient from one time to five times during a 24-hour period. In a preferred embodiment, sabcomeline is administered from one to three times during a 24-hour period. In another embodiment, from 50 micrograms to five milligrams of sabcomeline is used during a 24-hour period. In a preferred embodiment, from 150 micrograms to 450 micrograms of sabcomeline is used during a 24-hour period.

In one embodiment, milameline is used as the muscarinic Activator in combination with the muscarinic Inhibitor. In another embodiment, milameline is administered to a patient from one time to five times during a 24-hour period. In a preferred embodiment, milameline is administered from one to three times during a 24-hour period. In another embodiment, from 0.5 milligrams to 50 milligrams of milameline is used during a 24-hour period. In a preferred embodiment, from four milligrams to 16 milligrams of milameline is used during a 24-hour period.

In one embodiment, talsaclidine is used as the muscarinic Activator in combination with the muscarinic Inhibitor. In another embodiment, talsaclidine is administered to a patient from one time to five times during a 24-hour period. In a preferred embodiment, talsaclidine is administered from one to three times during a 24-hour period. In another embodiment, from five milligrams to 1 gram of talsaclidine is used during a 24-hour period. In a preferred embodiment, from 120 milligrams to 480 milligrams of talsaclidine is used during a 24-hour period.

In one embodiment, cevimeline is used as the muscarinic Activator in combination with the muscarinic Inhibitor. In another embodiment, cevimeline is administered to a patient from one time to five times during a 24-hour period. In a preferred embodiment, cevimeline is administered from one to three times during a 24-hour period. In another embodiment, from 45 milligrams to 750 milligrams of cevimeline is used during a 24-hour period. In a preferred embodiment, from 90 milligrams to 360 milligrams of cevimeline is used during a 24-hour period.

In one embodiment, pilocarpine is used as the muscarinic Activator in combination with the muscarinic Inhibitor. In another embodiment, pilocarpine is administered to a patient from one time to five times during a 24-hour period. In a preferred embodiment, pilocarpine is administered from one to three times during a 24-hour period. In another embodiment, from 7.5 milligrams to 500 milligrams of pilocarpine is used during a 24-hour period. In a preferred embodiment, from 30 milligrams to 200 milligrams of pilocarpine is used during a 24-hour period.

In one embodiment, trospium chloride is used as the muscarinic Inhibitor in combination with the muscarinic Activator. In another embodiment, trospium chloride is administered to a patient from one time to five times during a 24-hour period. In a preferred embodiment, trospium chloride is administered from one time to three times during a 24-hour period. In another embodiment, from five milligrams to 400 milligrams of trospium chloride is used during a 24-hour period. In a preferred embodiment, from 20 milligrams to 200 milligrams of trospium chloride is used during a 24-hour period.

In one embodiment, trospium chloride extended release is used as the muscarinic Inhibitor in combination with the muscarinic Activator. In another embodiment, trospium chloride extended release is administered to a patient from one time to five times during a 24-hour period. In a preferred embodiment, trospium chloride extended release is administered from one to three times during a 24-hour period. In another embodiment, from five milligrams to 400 milligrams of trospium chloride extended release is used during a 24-hour period. In a preferred embodiment, from 20 milligrams to 200 milligrams of trospium chloride extended release is used during a 24-hour period.

In one embodiment, solifenacin is used as the muscarinic Inhibitor in combination with the muscarinic Activator. In another embodiment, solifenacin is administered to a patient from one time to five times during a 24-hour period. In a preferred embodiment, solifenacin is administered from one time to three times during a 24-hour period. In another embodiment, from 0.25 milligrams to 100 milligrams of solifenacin is used during a 24-hour period. In a preferred embodiment, from 1 milligram to 30 milligrams of solifenacin is used during a 24-hour period.

In one embodiment, tolterodine is used as the muscarinic Inhibitor in combination with the muscarinic Activator. In another embodiment, tolterodine is administered to a patient from one time to five times during a 24-hour period. In a preferred embodiment, tolterodine is administered from one to three times during a 24-hour period. In another embodiment, from one milligram to 16 milligrams of tolterodine is used during a 24-hour period. In a preferred embodiment, from two milligrams to eight milligrams of tolterodine is used during a 24-hour period.

In one embodiment, fesoterodine is used as the muscarinic Inhibitor in combination with the muscarinic Activator. In another embodiment, fesoterodine is administered to a patient from one time to five times during a 24-hour period. In a preferred embodiment, fesoterodine is administered from one to three times during a 24-hour period. In another embodiment, from two milligrams to 56 milligrams of fesoterodine is used during a 24-hour period. In a preferred embodiment, from four milligrams to 28 milligrams of fesoterodine is used during a 24-hour period.

In one embodiment, darifenacin is used as the muscarinic Inhibitor in combination with the muscarinic Activator. In another embodiment, darifenacin is administered to a patient from one time to five times during a 24-hour period. In a preferred embodiment, darifenacin is administered from one to three times during a 24-hour period. In another embodiment, from 3.75 milligrams to 150 milligrams of darifenacin is used during a 24-hour period. In a preferred embodiment, from 7.5 milligrams to 30 milligrams of darifenacin is used during a 24-hour period.

While the subject is being treated, the health of the patient may be monitored by measuring one or more of the relevant indices at predetermined times during the treatment period. Treatment, including composition, amounts, times of administration and formulation, may be optimized according to the results of such monitoring. The patient may be periodically reevaluated to determine the extent of improvement by measuring the same parameters. Adjustments to the amount(s) of subject composition administered and possibly to the time of administration may be made based on these reevaluations.

Treatment may be initiated with smaller dosages that are less than the optimum dose of the compound. Thereafter, the dosage may be increased by small increments until the optimum balance between therapeutic effect and side effects is attained.

Dosage Forms of the Combination

In one embodiment, the muscarinic Activator and muscarinic Inhibitor are in different dosage forms or dosage vehicles. In a preferred embodiment, the muscarinic Activator and muscarinic Inhibitor are in the same dosage form or dosage vehicles. The dosage forms may include one or more pharmaceutically-acceptable carriers. The dosage forms may also include one or more pharmaceutically-acceptable salts. The dosage forms may be administered orally. The Activator and Inhibitor may be delivered orally using tablets, troches, liquids, emulsions, suspensions, drops, capsules, caplets or gel caps and other methods of oral administration known to one skilled in the art. The muscarinic Activator and Inhibitor may also be administered parentally. Other routes of administration include but are not limited to: topical, transdermal, nasal, ocular, rectal, sublingual, inhalation, and vaginal. For topical and transdermal administration, the Activator and Inhibitor may be delivered in a cream, gel, ointment, spray, suspension, emulsion, foam, or patch or by other methods known to one skilled in the art. For nasal administration, the Activator and Inhibitor may be delivered by sprays, drops, emulsions, foams, creams, ointments or other methods known to one skilled in the art. For nasal administration, formulations for inhalation may be prepared as an aerosol, either a solution aerosol in which the active agent is solubilized in a carrier, such as a propellant, or a dispersion aerosol, in which the active agent is suspended or dispersed throughout a carrier and an optional solvent. For ocular administration, the Activator and Inhibitor may be delivered in drops, sprays, injections, solutions, emulsions, suspensions, or ointments, or by other methods known to one skilled in the art. For rectal administration, the Activator and Inhibitor may be delivered using suppositories, enemas, creams, foams, gels, or ointments or by other methods known to one skilled in the art. For sublingual administration, the Activator and Inhibitor may be delivered in tablets, troches, liquids, emulsions, suspensions, drops, capsules, caplets or gel caps and by other methods of oral administration known to one skilled in the art. For administration by inhalation, the Activator and Inhibitor may be delivered in vapor, mist, powder, aerosol, or nebulized form, or by other methods known to one skilled in the art. For vaginal administration, the Activator and Inhibitor may be delivered in solutions, emulsions, suspensions, ointments, gels, foams, or vaginal rings or by other methods known to one skilled in the art.

The muscarinic Activator and Inhibitor may be in a dosage form that immediately releases the drug. In an alternative embodiment, the muscarinic Activator and Inhibitor are in a controlled release dosage form. In one embodiment of the controlled release dosage form, the Activator and Inhibitor have similar release kinetics. In another embodiment, the Inhibitor is released prior to the Activator's being released. In another embodiment, a three part release profile is used such that the Inhibitor is released immediately, followed by the Activator in a controlled release fashion and then by the Inhibitor in a controlled release fashion. In one embodiment, the muscarinic Activator and Inhibitor are packaged in liposomes. In a further embodiment, the liposome comprises a phospholipid. In a further embodiment, the phospholipid in the liposome is selected from phosphatidylcholine (PC), phosphatidylglycerol (PG), phosphatidylinositol (PI), phosphatidylserine (PS), phosphatidylethanolamine (PE), phosphatidic acid (PA), egg phosphatidylcholine (EPC), egg phosphatidylglycerol (EPG), egg phosphatidylinositol (EPI), egg phosphatidylserine (EPS), egg phosphatidylethanolamine (EPE), egg phosphatidic acid (EPA), soy phosphatidylcholine (SPC), soy phosphatidylglycerol (SPG), soy phosphatidylserine (SPS), soy phosphatidylinositol (SPI), soy phosphatidylethanolamine (SPE), soy phosphatidic acid (SPA), hydrogenated egg phosphatidylcholine (HEPC), hydrogenated soy phosphatidylcholine (HSPC), dipalmitoylphosphatidylcholine (DPPC), dioleoylphosphatidylcholine (DOPC), dimyristoylphosphatidylcholine (DMPC), dimyristoylphosphatidylglycerol (DMPG), dipalmitoylphosphatidylglycerol (DPPG), distearoylphosphatidylcholine (DSPQ), distearoylphosphatidylglycerol (DSPG), dioleoylphosphatidyl-ethanolamine (DOPE), palmitoylstearoylphosphatidyl-choline (PSPC), palmitoyl-stearolphosphatidylglycerol (PSPG), mono-oleoyl-phosphatidylethanolamine (MOPE), dilauroyl ethylphosphocholine (DLEP), dimyristoyl ethylphosphocholine (DMEP), dipalmitoyl ethylphosphocholine (DPEP), distearoyl ethylphosphocholine (DSEP), dimyristoylphosphatidic acid (DMPA), dipalmitoylphosphatidic acid (DPPA), distearoylphosphatidic acid (DSPA), dimyristoylphosphatidylinositol (DMPI), dipalmitoylphosphatidylinositol (DPPI), distearoylphosphatidylinositol (DSPI), dimyristoylphosphatidylserine (DMPS), dipalmitoylphosphatidylserine (DPPS), distearoylphosphatidylserine (DSPS), N-acylated phosphorylethanolamine (NAPE), and combinations thereof.

In a further embodiment, the controlled release formulation comprises a semi-permeable membrane. The muscarinic Activator and muscarinic Inhibitor may be in different membranes in the same formulation. In another embodiment, the muscarinic Activator and muscarinic Inhibitor can be in different membranes in different formulations or dosing vehicles. In a further embodiment, the semi-permeable membrane comprises a polymer. In a further embodiment, the controlled release formulation comprises a matrix that suspends the muscarinic Activator(s) and muscarinic Inhibitor(s). The muscarinic Activator and Inhibitor may be in separate matrices within the same medicament. In a further embodiment, the matrix comprises a polymer. In a further embodiment, the polymer comprises a water-soluble polymer. In a further embodiment, the water-soluble polymer is selected from Eudragit RL, polyvinyl alcohol, polyvinylpyrrolidone, methyl cellulose, hydroxypropyl cellulose, hydroxypropylmethyl cellulose, polyethylene glycol, and mixtures thereof. In a further embodiment, the polymer comprises a water insoluble polymer. In a further embodiment, the water insoluble polymer is selected from Eudragit RS, ethylcellulose, cellulose acetate, cellulose propionate, cellulose acetate propionate, cellulose acetate butyrate, cellulose acetate phthalate, cellulose triacetate, poly(methyl methacrylate), poly(ethyl methacrylate), poly(butyl methacrylate), poly(isobutylmethacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), poly(ethylene), poly(ethylene) low density, poly(ethylene) high density, poly(propylene), poly(ethylene terephthalate), poly(vinyl isobutyl ether), poly(vinyl acetate), poly(vinyl chloride), polyurethane, and mixtures thereof. In a further embodiment, the matrix comprises a fatty compound. In a further embodiment, the fatty compound is a wax or glyceryl tristearate. In a further embodiment, the polymer comprises a water-soluble polymer and a water insoluble polymer. In a further embodiment, the matrix further comprises a fatty compound.

The muscarinic Activator and muscarinic Inhibitor may be in dosage forms that use other methods of controlled release formulation known to one skilled in the art (for example, Dixit & Puthli. *J Control Release*. 2:94. 2009; Mizrahi & Domb. *Recent Pat Drug Deliv Formul*. 2:108. 2008; Forqueri & Singh. *Recent Pat Drug Deliv Formul*. 3:40. 2009; Kalantzi et al. *Recent Pat Drug Deliv Formul*. 3:49. 2009; Iconomopoulou et al. *Recent Pat Drug Deliv Formul*. 2:94. 2008; Panos et al. *Curr Drug Discov Technol*. 5: 333. 2008; 2008. Wan et al. *Nanomed*. 2:483. 2007. Wang et al. *Drug Delivery: Principles & Applications*. Wiley 2005).

In another embodiment, the combination of the muscarinic Activator and Inhibitor is used in combination with one or more therapies that can include both psychotherapy and drugs. Therapeutic agents include but are not limited to antipsychotics, anxiolytics, anti-depressants, sedatives, tranquilizers and other pharmacological interventions known to one skilled in the art. A therapeutic agent may fall under the category of more than one type of drug. For instance, benzodiazepines can be considered anxiolytics, sedatives and tranquilizers.

Medicament Containing One or More Muscarinic Activators & Muscarinic Inhibitors

One embodiment of the invention is a medicament comprising one or more muscarinic Activators and one or more muscarinic Inhibitors.

In one embodiment, from 10 micrograms to 10 grams of Activator is used in the combination with the Inhibitor in the medicament. In another embodiment, from 1 milligram to 1 gram of Activator is used in the combination with the Inhibitor. In another embodiment from 10 micrograms to 10 grams of Inhibitor is used in the combination with the Activator. In another embodiment, from 1 milligram to 1 gram of Inhibitor is used in the combination with the Activator.

In one embodiment, the medicament is administered to a patient 6 times during a 24-hour period. In another embodiment, the medicament is administered to a patient 5 times during a 24-hour period. In another embodiment, the medicament is administered to a patient 4 times during a 24-hour period. In another embodiment, the medicament is administered to a patient 3 times during a 24-hour period. In another embodiment, the medicament is administered to a patient 2 times during a 24-hour period. In another embodiment, the medicament is administered to a patient one time during a 24-hour period. In a preferred embodiment, the medicament is administered from one to 3 times during a 24-hour period.

In one embodiment of the invention, the medicament contains a combination of a muscarinic Activator and a muscarinic Inhibitor with a theta score of 230 or greater as determined by in silico testing using the above described algorithm. In another embodiment of the invention, the medicament contains a combination of a muscarinic Activator and a muscarinic Inhibitor with a theta score of 200 or greater as determined by in silico testing using the above described algorithm. In another embodiment of the invention, the medicament contains a combination of a muscarinic Activator and a muscarinic Inhibitor with a theta score of 150 or greater as determined by in silico testing using the above described algorithm. In a further embodiment of the invention, the medicament contains a combination of a muscarinic Activator and a muscarinic Inhibitor with a theta score of 149 or lower as determined by in silico testing using the above described algorithm. In a further embodiment, xanomeline is used as the muscarinic Activator in the medicament. In another embodiment, the medicament contains from five milligrams to 700 milligrams of xanomeline. In a preferred embodiment, the medicament contains from 25 milligrams to 300 milligrams of xanomeline.

In one embodiment, sabcomeline is used as the muscarinic Activator in the medicament. In another embodiment, the medicament contains from 10 micrograms to five milligrams of sabcomeline. In a preferred embodiment, the medicament contains from 50 micrograms to 450 micrograms of sabcomeline.

In one embodiment, milameline is used as the muscarinic Activator in the medicament. In another embodiment, the medicament contains from 0.1 milligrams to 50 milligrams of milameline. In a preferred embodiment, the medicament contains from one milligram to 16 milligrams of milameline.

In one embodiment, talsaclidine is used as the muscarinic Activator in the medicament. In another embodiment, the medicament contains from one milligram to one gram of talsaclidine. In a preferred embodiment, the medicament contains from 40 milligrams to 480 milligrams of talsaclidine.

In one embodiment, cevimeline is used as the muscarinic Activator in the medicament. In another embodiment, the medicament contains from nine milligrams to 750 milligrams of cevimeline. In a preferred embodiment, the medicament contains from 30 milligrams to 360 milligrams of cevimeline.

In one embodiment, pilocarpine is used as the muscarinic Activator in the medicament. In another embodiment, the medicament contains from 1.5 milligrams to 500 milligrams of pilocarpine. In a preferred embodiment, the medicament contains from 10 milligrams to 200 milligrams of pilocarpine.

In one embodiment, trospium chloride is used as the muscarinic Inhibitor in the medicament. In another embodiment, the medicament contains from one milligram to 400 milligrams of trospium chloride. In a preferred embodiment, the medicament contains from 6.5 milligrams to 200 milligrams of trospium chloride.

In one embodiment, trospium chloride extended release is used as the muscarinic Inhibitor in the medicament. In another embodiment, the medicament contains from one milligram to 400 milligrams of trospium chloride extended release. In a preferred embodiment, the medicament contains from 6.5 milligrams to 200 milligrams of trospium chloride extended release.

In one embodiment, solifenacin is used as the muscarinic Inhibitor in the medicament. In another embodiment, the medicament contains from 0.25 milligram to 100 milligrams of solifenacin. In a preferred embodiment, the medicament contains from 1 milligrams to 30 milligrams of solifenacin.

In one embodiment, tolterodine is used as the muscarinic Inhibitor in the medicament. In another embodiment, the medicament contains from 0.2 milligrams to 16 milligrams of tolterodine. In a preferred embodiment, the medicament contains from 0.7 milligrams to eight milligrams of tolterodine.

In one embodiment, fesoterodine is used as the muscarinic Inhibitor in the medicament. In another embodiment, the medicament contains from 0.4 milligrams to 56 milligrams of fesoterodine. In a preferred embodiment, the medicament contains between one milligrams to 28 milligrams of fesoterodine.

In one embodiment, darifenacin is used as the muscarinic Inhibitor in the medicament. In another embodiment, the medicament contains from n 0.8 milligrams to 150 milligrams of darifenacin. In a preferred embodiment, the medicament contains from 2.5 milligrams to 30 milligrams of darifenacin.

While the subject is being treated, the health of the patient may be monitored by measuring one or more of the relevant indices at predetermined times during the treatment period. Treatment, including composition, amounts, times of administration and formulation, may be optimized according to the results of such monitoring. The patient may be periodically reevaluated to determine the extent of improvement by measuring the same parameters. Adjustments to the amount(s) of subject composition administered and possibly to the time of administration may be made based on these reevaluations.

Treatment may be initiated with smaller dosages that are less than the optimum dose of the compound. Thereafter, the dosage may be increased by small increments until the optimum balance between therapeutic effect and side effects is attained. This principle of drug titration is well understood by those of skill in the art.

The medicament may also include one or more pharmaceutically-acceptable salts. The medicament may include one or more pharmaceutically-acceptable carriers. The medicament may be administered orally. The medicament may be delivered orally using tablets, troches, liquids, emulsions, suspensions, drops, capsules, caplets or gel caps and other methods of oral administration known to one skilled in the art. The medicament may also be administered parentally. Other routes of administration include but are not limited to: topical, transdermal, nasal, rectal, ocular, sublingual, inhalation, and vaginal. For topical and transdermal administration, the medicament may be delivered in a cream, gel, ointment, spray, suspension, emulsion, foam, or patch or by other methods known to one skilled in the art. For nasal administration, the medicament may be delivered by sprays, drops, emulsions, foams, creams, or ointments or by other methods known to one skilled in the art. For nasal administration, formulations for inhalation may be prepared as an aerosol, either a solution aerosol in which the active agent is solubilized in a carrier, such as a propellant, or a dispersion aerosol, in which the active agent is suspended or dispersed throughout a carrier and an optional solvent. For rectal administration, the medicament may be delivered using suppositories, enemas, creams, foams, gels, or ointments or by other methods known to one skilled in the art. For ocular administration, the medicament may be delivered in drops, sprays, injections, solutions, emulsions, suspensions, or ointments, or by other methods known to one skilled in the art. For sublingual administration, the medicament may be delivered in tablets, troches, liquids, emulsions, suspensions, drops, capsules, caplets or gel caps and by other methods of oral administration known to one skilled in the art. For administration by inhalation, the medicament may be delivered in vapor, mist, powder, aerosol, or nebulized form, or by other methods known to one skilled in the art. For vaginal administration, the medicament may be delivered in solutions, emulsions, suspensions, ointments, gels, foams, or vaginal rings or by other methods known to one skilled in the art.

The medicament may be in a dosage form that immediately releases the drug. In an alternative embodiment, the medicament may have a controlled release dosage form. In one embodiment, the medicament is packaged in liposomes. In a further embodiment, the liposome comprises a phospholipid. In a further embodiment, the phospholipid in the liposome is selected from phosphatidylcholine (PC), phosphatidylglycerol (PG), phosphatidylinositol (PI), phosphatidylserine (PS), phosphatidylethanolamine (PE), phosphatidic acid (PA), egg phosphatidylcholine (EPC), egg phosphatidylglycerol (EPG), egg phosphatidylinositol (EPI), egg phosphatidylserine (EPS), egg phosphatidylethanolamine (EPE), egg phosphatidic acid (EPA), soy phosphatidylcholine (SPC), soy phosphatidylglycerol (SPG), soy phosphatidylserine (SPS), soy phosphatidylinositol (SPI), soy phosphatidylethanolamine (SPE), soy phosphatidic acid (SPA), hydrogenated egg phosphatidylcholine (HEPC), hydrogenated soy phosphatidylcholine (HSPC), dipalmitoylphosphatidylcholine (DPPC), dioleoylphosphatidylcholine (DOPC), dimyristoylphosphatidylcholine (DMPC), dimyristoylphosphatidylglycerol (DMPG), dipalmitoylphosphatidylglycerol (DPPG), distearoylphosphatidylcholine (DSPQ), distearoylphosphatidylglycerol (DSPG), dioleoylphosphatidyl-ethanolamine (DOPE), palmitoylstearoylphosphatidyl-choline (PSPC), palmitoylstearolphosphatidylglycerol (PSPG), mono-oleoyl-phosphatidylethanolamine (MOPE), dilauroyl ethylphosphocholine (DLEP), dimyristoyl ethylphosphocholine (DMEP), dipalmitoyl ethylphosphocholine (DPEP), distearoyl ethylphosphocholine (DSEP), dimyristoylphosphatidic acid (DMPA), dipalmitoylphosphatidic acid (DPPA), distearoylphosphatidic acid (DSPA), dimyristoylphosphatidylinositol (DMPI), dipalmitoylphosphatidylinositol (DPPI), distearoylphosphatidylinositol (DSPI), dimyristoylphosphatidylserine (DMPS), dipalmitoylphosphatidylserine (DPPS), distearoylphosphatidylserine (DSPS), N-acylated phosphorylethanolamine (NAPE), and combinations thereof.

In a further embodiment, the controlled release formulation comprises a semi-permeable membrane. The muscarinic Activator and muscarinic Inhibitor may be in different membranes in the same formulation. In another embodiment, the muscarinic Activator and muscarinic Inhibitor can be in different membranes in different formulations or dosing vehicles. In a further embodiment, the semi-permeable membrane comprises a polymer. In a further embodiment, the controlled release formulation comprises a matrix that suspends the muscarinic Activator(s) and Inhibitor(s). The muscarinic Activator and Inhibitor may be in separate matrices within the same medicament. In a further embodiment, the matrix comprises a polymer. In a further embodiment, the polymer comprises a water-soluble polymer. In a further embodiment, the water-soluble polymer is selected from Eudragit RL, polyvinyl alcohol, polyvinylpyrrolidone, methyl cellulose, hydroxypropyl cellulose, hydroxypropylmethyl cellulose, polyethylene glycol, and mixtures thereof. In a further embodiment, the polymer comprises a water insoluble polymer. In a further embodiment, the water insoluble polymer is selected from Eudragit RS, ethylcellulose, cellulose acetate, cellulose propionate, cellulose acetate propionate, cellulose acetate butyrate, cellulose acetate phthalate, cellulose triacetate, poly(methyl methacrylate), poly(ethyl methacrylate), poly(butyl methacrylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), poly(ethylene), poly(ethylene) low density, poly(ethylene) high density, poly(propylene), poly(ethylene terephthalate), poly(vinyl isobutyl ether), poly(vinyl acetate), poly(vinyl chloride), polyurethane, and a mixtures thereof. In a further embodiment, the matrix comprises a fatty compound. In a further embodiment, the fatty compound is a wax or glyceryl tristearate. In a further embodiment, the polymer comprises a water-soluble polymer and a water insoluble polymer. In a further embodiment, the matrix further comprises a fatty compound.

The medicament may be in dosage forms that use other methods of controlled release formulation known to one in the art (for example, Dixit & Puthli. *J Control Release.* 2:94. 2009; Mizrahi & Domb. *Recent Pat Drug Deliv Formul.* 2:108. 2008; Forqueri & Singh. *Recent Pat Drug Deliv Formul.* 3:40. 2009; Kalantzi et al. *Recent Pat Drug Deliv Formul.* 3:49. 2009; Iconomopoulou et al. *Recent Pat Drug Deliv Formul.* 2:94. 2008; Panos et al. *Curr Drug Discov Technol.* 5: 333. 2008; Wan et al. *Nanomed.* 2:483. 2007. Wang et al. *Drug Delivery: Principles & Applications.* Wiley 2005).

In another embodiment, the medicament is used in combination with one or more therapies that can include both psychotherapy and drugs. Therapeutic agents include but are not limited to antipsychotics, anxiolytics, anti-depressants, sedatives, tranquilizers and other pharmacological interventions known to one skilled in the art. A therapeutic agent may fall under the category of more than one type of drug. For instance, benzodiazepines can be considered anxiolytics, sedatives and tranquilizers.

The above-described benefits of the novel methods and compositions of the present invention are illustrated by the non-limiting examples that follow.

EXAMPLES

Example 1

In one example, the invention is a single capsule formulation containing 75 milligrams of xanomeline and 20 milligrams of trospium chloride. The capsule consists of a gelatin shell surrounding a fill material composed of the active compounds, a vehicle, a surfactant and a modifier. The vehicle is polyethylene glycol with a molecular weight in the range of from 500 to 10,000 Daltons and is 10% of the fill material by weight. The surfactant is polysorbate 80 and represents 0.1% by weight of the fill material. The modifier is fumed silica present at 0.25% by weight of the fill material. The total fill material represents 50% of the total capsule weight and the gelatin shell is 50% of the total capsule weight.

Example 2

A second formulation is the capsule in Example 1 with an additional outer controlled release layer comprising an enteric material (material that is relatively insoluble in the acidic environment of the stomach). There are a variety of enteric materials known to one skilled in the art. For this specific formulation we use hydroxyethylcellulose which would compose 20% of total capsule weight.

Example 3

A third example is a formulation prepared as in Example 2, with the capsule containing 225 mg of xanomeline and 60 milligrams of trospium chloride.

Example 4

In one example, the invention is a single capsule formulation containing 75 milligrams of xanomeline and 5 milligrams of solifenacin. The capsule consists of a gelatin shell surrounding a fill material composed of the active compounds, a vehicle, a surfactant and a modifier. The vehicle is polyethylene glycol with a molecular weight in the range of from 500 to 10,000 Daltons and is 10% of the fill material by weight. The surfactant is polysorbate 80 and represents 0.1% by weight of the fill material. The modifier is fumed silica present at 0.25% by weight of the fill material. The total fill material represents 50% of the total capsule weight and the gelatin shell is 50% of the total capsule weight.

Example 5

A second formulation is the capsule in Example 41 with an additional outer controlled release layer comprising an enteric material (material that is relatively insoluble in the acidic environment of the stomach). There are a variety of enteric materials known to one skilled in the art. For this specific formulation we use hydroxyethylcellulose which would compose 20% of total capsule weight.

Example 6

A third example is a formulation prepared as in Example 52, with the capsule containing 225 mg of xanomeline and 10 milligrams of solifenacin.

REFERENCES

All publications and patents mentioned herein are hereby incorporated by reference in their entirety as if each individual publication or patent was specifically and individually incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present invention.

We claim:

1. A single capsule formulation for oral administration comprising xanomeline and/or a salt thereof in an amount to cause a side effect chosen from nausea, vomiting, diarrhea, sweating and excess salivation; and trospium chloride in an amount effective to reduce the side effect associated with the oral administration of the xanomeline and/or the salt thereof.

2. The formulation of claim 1, which is formulated as an immediate release formulation.

3. The formulation of claim 1, which is formulated as a controlled release formulation.

4. The formulation of claim 1, wherein the xanomeline and/or the salt thereof is formulated as a controlled release formulation and the trospium chloride is formulated as an immediate release formulation.

5. The formulation of claim 1, wherein the formulation contains from 1 milligram to 1 gram of xanomeline and/or the salt thereof.

6. The formulation of claim 1, wherein the formulation contains from five milligrams to 700 milligrams of xanomeline and/or the salt thereof.

7. The formulation of claim 1, wherein the formulation contains from five milligrams to 500 milligrams of xanomeline and/or the salt thereof.

8. The formulation of claim 1, wherein the formulation contains from 25 milligrams to 300 milligrams of xanomeline and/or the salt thereof.

9. The formulation of claim 1, wherein the formulation contains from one milligram to 400 milligrams of trospium chloride.

10. The formulation of claim 1, wherein the formulation contains from 6.5 milligrams to 200 milligrams of trospium chloride.

11. The formulation of claim 1, wherein the formulation contains 20 milligrams of trospium chloride.

12. A method of treating schizophrenia in a patient in need thereof, the method comprising:
orally administering a single capsule formulation of claim 1 twice daily.

13. The method of claim 12, wherein the formulation contains 20 milligrams of trospium chloride.

14. The method of claim 12, wherein the formulation contains from 25 milligrams to 300 milligrams of xanomeline and/or the salt thereof.

15. The formulation of claim 1, wherein the salt of xanomeline is the salt of tartaric acid.

16. The formulation of claim 1, wherein the amount of the xanomeline and/or the salt thereof is effective to treat a central nervous system disorder chosen from Alzheimer's disease, Huntington's disease, Parkinson's disease, and Lewy Body dementia.

* * * * *